United States Patent
Mao et al.

(10) Patent No.: US 9,713,443 B2
(45) Date of Patent: *Jul. 25, 2017

(54) BIOSENSOR MEMBRANES

(71) Applicant: Abbott Diabetes Care Inc., Alameda, CA (US)

(72) Inventors: Fei Mao, Fremont, CA (US); Hyun Cho, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,403

(22) Filed: Aug. 15, 2016

(65) Prior Publication Data

US 2017/0027489 A1    Feb. 2, 2017

Related U.S. Application Data

(63) Continuation of application No. 14/691,239, filed on Apr. 20, 2015, now Pat. No. 9,414,778, which is a
(Continued)

(51) Int. Cl.
*A61B 5/05*     (2006.01)
*A61B 5/1486*   (2006.01)
(Continued)

(52) U.S. Cl.
CPC ........ *A61B 5/14865* (2013.01); *A61B 5/1473* (2013.01); *A61B 5/14532* (2013.01);
(Continued)

(58) Field of Classification Search
CPC .. C12Q 1/006; A61B 5/14532; A61B 5/14865
See application file for complete search history.

(56) References Cited

U.S. PATENT DOCUMENTS 4,340,457 A    7/1982  Kater
4,436,094 A    3/1984  Cerami
(Continued)

FOREIGN PATENT DOCUMENTS

EP    0352610    1/1990
GB    2209836    5/1989
(Continued)

OTHER PUBLICATIONS

Bourdillon et al. (1995) "Catalysis and Mass Transport in Spatially Ordered Enzyme Assemblies on Electrodes" *J Am Chem Soc* 117:11499-11506.
(Continued)

*Primary Examiner* — Christian Jang
(74) *Attorney, Agent, or Firm* — Edward J. Baba; Khin K. Chin; Bozicevic, Field & Francis LLP

(57) ABSTRACT

Novel membranes comprising various polymers containing heterocyclic nitrogen groups are described. These membranes are usefully employed in electrochemical sensors, such as amperometric biosensors. More particularly, these membranes effectively regulate a flux of analyte to a measurement electrode in an electrochemical sensor, thereby improving the functioning of the electrochemical sensor over a significant range of analyte concentrations. Electrochemical sensors equipped with such membranes are also described.

20 Claims, 11 Drawing Sheets

Related U.S. Application Data continuation of application No. 13/862,157, filed on Apr. 12, 2013, now Pat. No. 9,014,774, which is a continuation of application No. 12/544,819, filed on Aug. 20, 2009, now Pat. No. 8,437,829, which is a continuation of application No. 11/174,222, filed on Jul. 1, 2005, now Pat. No. 7,670,470, which is a continuation of application No. 10/146,518, filed on May 14, 2002, now Pat. No. 6,932,894.

(60) Provisional application No. 60/291,215, filed on May 15, 2001.

(51) Int. Cl.
| | | |
|---|---|---|
| *C12Q 1/00* | (2006.01) | |
| *A61B 5/145* | (2006.01) | |
| *A61B 5/00* | (2006.01) | |
| *A61B 5/1473* | (2006.01) | |

(52) U.S. Cl.
CPC ........ *A61B 5/14546* (2013.01); *A61B 5/6846* (2013.01); *C12Q 1/002* (2013.01); *C12Q 1/004* (2013.01); *C12Q 1/006* (2013.01)

(56) References Cited

U.S. PATENT DOCUMENTS

| | | |
|---|---|---|
| 4,534,355 A | 8/1985 | Potter |
| 4,703,756 A | 11/1987 | Gough et al. |
| 4,891,104 A | 1/1990 | Liston et al. |
| 4,929,313 A | 5/1990 | Wrighton |
| 4,943,364 A | 7/1990 | Koch et al. |
| 4,974,929 A | 12/1990 | Curry |
| 5,165,407 A | 11/1992 | Wilson et al. |
| 5,200,051 A | 4/1993 | Cozzette et al. |
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |
| 5,543,326 A | 8/1996 | Heller et al. |
| 5,593,852 A | 1/1997 | Heller et al. |
| 5,605,152 A | 2/1997 | Slate et al. |
| 5,611,900 A | 3/1997 | Worden et al. |
| 5,665,222 A | 9/1997 | Heller et al. |
| 5,696,314 A | 12/1997 | McCaffrey et al. |
| 5,773,270 A | 6/1998 | D'Orazio et al. |
| 5,804,048 A | 9/1998 | Wong et al. |
| 5,882,494 A | 3/1999 | Van Antwerp |
| 5,964,993 A | 10/1999 | Blubaugh et al. |
| 5,972,199 A | 10/1999 | Heller et al. |
| 6,015,480 A | 1/2000 | Craig et al. |
| 6,103,033 A | 8/2000 | Say et al. |
| 6,119,028 A | 9/2000 | Schulman et al. |
| 6,120,676 A | 9/2000 | Heller et al. |
| 6,134,461 A | 10/2000 | Say et al. |
| 6,143,164 A | 11/2000 | Heller et al. |
| 6,175,752 B1 | 1/2001 | Say et al. |
| 6,338,790 B1 | 1/2002 | Feldman et al. |
| 6,368,274 B1 | 4/2002 | Van Antwerp et al. |
| 6,484,045 B1 | 11/2002 | Holker et al. |
| 6,592,746 B1 | 7/2003 | Schmid-Schoenbein |
| 6,642,015 B2 | 11/2003 | Vachon et al. |
| 6,746,582 B2 | 6/2004 | Heller et al. |
| 6,932,894 B2 | 8/2005 | Mao et al. |
| 6,975,893 B2 | 12/2005 | Say et al. |
| 7,670,470 B2 | 3/2010 | Mao et al. |
| 8,147,666 B2 | 4/2012 | Mao et al. |
| 8,437,829 B2 | 5/2013 | Mao et al. |
| 2001/0039393 A1 | 11/2001 | Mori et al. |
| 2001/0051768 A1 | 12/2001 | Schulman et al. |
| 2001/0054319 A1 | 12/2001 | Heller et al. |
| 2003/0077772 A1 | 4/2003 | Shah et al. |
| 2003/0078560 A1 | 4/2003 | Miller et al. |
| 2004/0064133 A1 | 4/2004 | Miller et al. |
| 2004/0074785 A1 | 4/2004 | Holker et al. |
| 2005/0031689 A1 | 2/2005 | Shults et al. |
| 2005/0033132 A1 | 2/2005 | Shults et al. |
| 2007/0173710 A1 | 7/2007 | Petisce et al. |
| 2007/0244379 A1 | 10/2007 | Boock et al. |

FOREIGN PATENT DOCUMENTS

| | | |
|---|---|---|
| JP | 61-123611 | 6/1986 |
| JP | 1-235593 | 9/1989 |
| JP | 75-06675 | 7/1995 |
| WO | WO 94/10553 | 5/1994 |
| WO | WO 01/36660 | 5/2001 |
| WO | WO 01/57241 | 8/2001 |
| WO | WO 03/085372 | 10/2003 |

OTHER PUBLICATIONS

Caruso et al. (1997) "Assembly of Alternating Polyelectrolyte and Protein Multilayer Films for Immunosensing" *Langmuir* 13(13):3427-3433.

Kabanov et al. (1996) "Interaction of polyions with cell-mimetic species: Physico-chemical and biomedical aspects" *Journal of Controlled Release* 39:173-189.

Kobayashi et al. (1999) "Alternate Deposition of Cationic and Anionic Polymers for the Improvement of Response Characteristics of Glucose Biosensor" *Electrochemistry* 67(12):1147-1149.

Lvov et al. (1995) "Assembly of Multicomponent Protein Films by Means of Electrostatic Layer-by-Layer Adsorption" *J Am Chem Soc* 117:6117-6123.

Ohara et al. (1993) "Glucose Electrodes Based on Cross-Linked Os(bpy)2Cl)+/2+ Complexed Poly(1-vinylimidazole) Films" *Anal Chem* 65:3512-3517.

Osha Guideline for Ethylamine downloaded from www.osha.gov on Jul. 2, 2009.

Sullivan et al. (1985) "Chemistry of Highly Reduced Polypyridyl-Metal Complexes. Anion Substitution Induced by Ligand-Based Reduction" *Inorg Chem* 24:3640-3645.

Sun et al. (1998) "Chemically modified electrode via layer-by-layer deposition of glucose oxidase (GOD) and polycation-bearing Os complex" *Thin Solid Films* 327-329:730-733.

Vuillaume et al. (2000) "Synthesis and Solid-State Characterization of Amphiphilic Tail-End Pyridinium Polymethacrylates" *Macromolecules* 33:781-790.

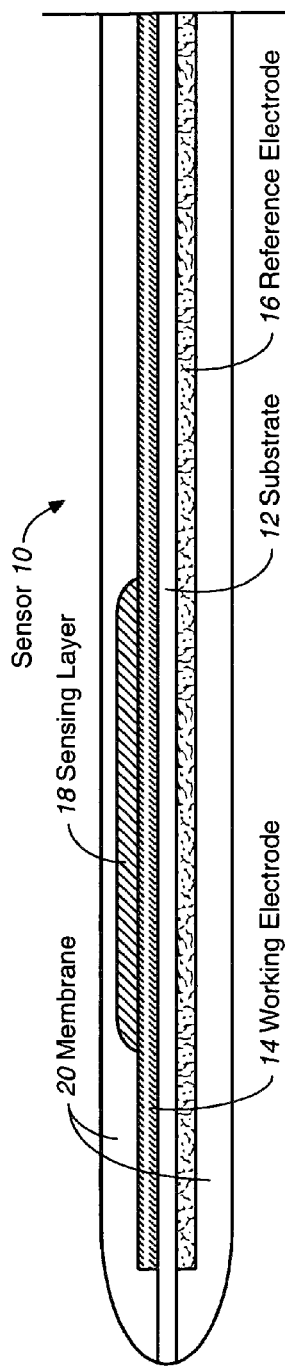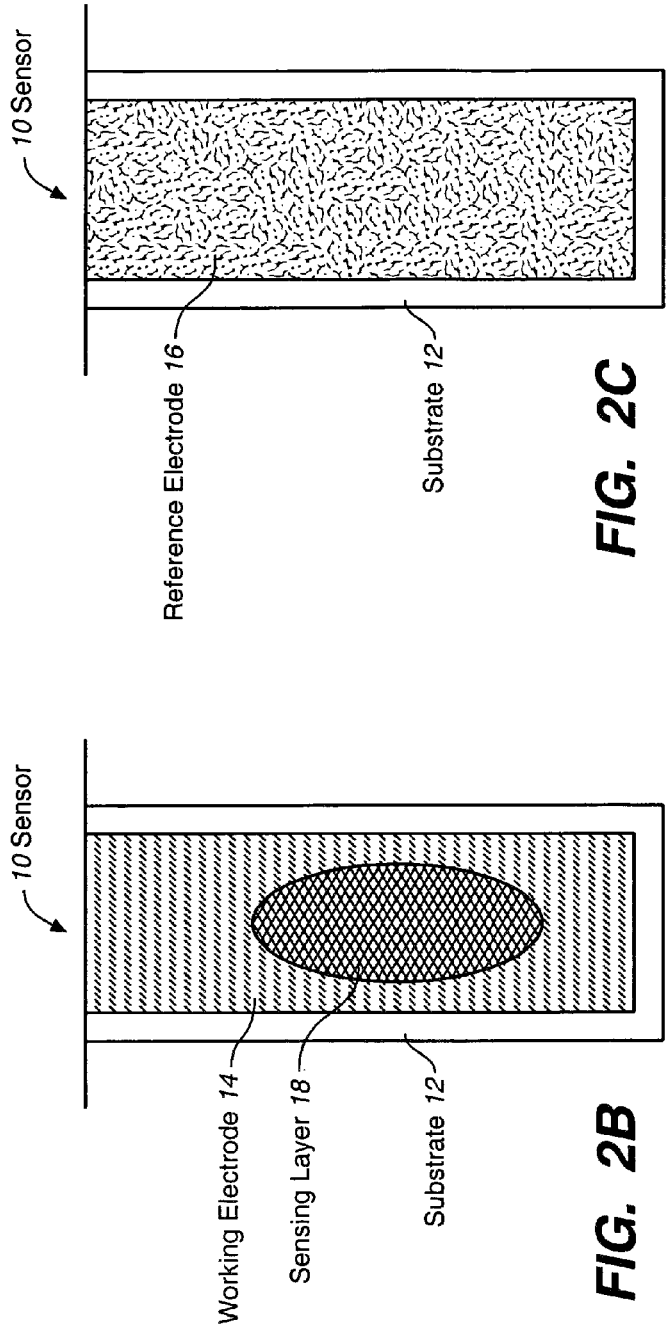
FIG. 2A
FIG. 2B
FIG. 2C

BIOSENSOR MEMBRANES

CROSS-REFERENCE TO RELATED APPLICATIONS

This application is a continuation of U.S. patent application Ser. No. 14/691,239, filed on Apr. 20, 2015, now U.S. Pat. No. 9,414,778, which is a continuation of U.S. patent application Ser. No. 13/862,157, filed on Apr. 12, 2013, now U.S. Pat. No. 9,014,774, which is a continuation of U.S. patent application Ser. No. 12/544,819, filed on Aug. 20, 2009, now U.S. Pat. No. 8,437,829, which is a continuation of U.S. patent application Ser. No. 11/174,222, filed on Jul. 1, 2005, now U.S. Pat. No. 7,670,470, which is a continuation of U.S. patent application Ser. No. 10/146,518, filed on May 14, 2002, now U.S. Pat. No. 6,932,894, which claims the benefit of U.S. Provisional Application Ser. No. 60/291,215 of Fei Mao, filed on May 15, 2001 and entitled "Biosensor Membranes Composed of Polyvinylpyridines", which are incorporated by reference herein in their entirety.

FIELD OF THE INVENTION

This invention generally relates to an analyte-flux-limiting membrane. More particularly, the invention relates to such a membrane composed of polymers containing heterocyclic nitrogens. The membrane is a useful component in biosensors, and more particularly, in biosensors that can be implanted in a living body.

BACKGROUND OF THE INVENTION

Enzyme-based biosensors are devices in which an analyte-concentration-dependent biochemical reaction signal is converted into a measurable physical signal, such as an optical or electrical signal. Such biosensors are widely used in the detection of analytes in clinical, environmental, agricultural and biotechnological applications. Analytes that can be measured in clinical assays of fluids of the human body include, for example, glucose, lactate, cholesterol, bilirubin and amino acids. The detection of analytes in biological fluids, such as blood, is important in the diagnosis and the monitoring of many diseases.

Biosensors that detect analytes via electrical signals, such as current (amperometric biosensors) or charge (coulometric biosensors), are of special interest because electron transfer is involved in the biochemical reactions of many important bioanalytes. For example, the reaction of glucose with glucose oxidase involves electron transfer from glucose to the enzyme to produce gluconolactone and reduced enzyme. In an example of an amperometric glucose biosensor, glucose is oxidized by oxygen in the body fluid via a glucose oxidase-catalyzed reaction that generates gluconolactone and hydrogen peroxide, whereupon the hydrogen peroxide is electrooxidized and correlated to the concentration of glucose in the body fluid. (Thomé-Duret, V., et al., Anal. Chem. 68, 3822 (1996); and U.S. Pat. No. 5,882,494 of Van Antwerp.) In another example of an amperometric glucose biosensor, the electrooxidation of glucose to gluconolactone is mediated by a polymeric redox mediator that electrically "wires" the reaction center of the enzyme to an electrode. (Csöregi, E., et al., Anal. Chem. 66, 3131 (1994); Csöregi, E., et al., Anal. Chem. 67, 1240 (1995); Schmidtke, D. W., et al., Anal. Chem. 68, 2845 (1996); Schmidtke, D. W., et al., Anal. Chem. 70, 2149 (1998); and Schmidtke, D. W., et al., Proc. Natl. Acad. Sci. U.S.A. 95, 294 (1998).)

Amperometric biosensors typically employ two or three electrodes, including at least one measuring or working electrode and one reference electrode. In two-electrode systems, the reference electrode also serves as a counter-electrode. In three-electrode systems, the third electrode is a counter-electrode. The measuring or working electrode is composed of a non-corroding carbon or a metal conductor and is connected to the reference electrode via a circuit, such as a potentiostat.

Some biosensors are designed for implantation in a living animal body, such as a mammalian or a human body, merely by way of example. In an implantable amperometric biosensor, the working electrode is typically constructed of a sensing layer, which is in direct contact with the conductive material of the electrode, and a diffusion-limiting membrane layer on top of the sensing layer. The sensing layer typically consists of an enzyme, an enzyme stabilizer such as bovine serum albumin (BSA), and a crosslinker that crosslinks the sensing layer components. Alternatively, the sensing layer consists of an enzyme, a polymeric mediator, and a crosslinker that crosslinks the sensing layer components, as in the above-mentioned "wired-enzyme" biosensor.

In an implantable amperometric glucose sensor, the membrane is often beneficial or necessary for regulating or limiting the flux of glucose to the sensing layer. By way of explanation, in a glucose sensor without a membrane, the flux of glucose to the sensing layer increases linearly with the concentration of glucose. When all of the glucose arriving at the sensing layer is consumed, the measured output signal is linearly proportional to the flux of glucose and thus to the concentration of glucose. However, when the glucose consumption is limited by the kinetics of chemical or electrochemical activities in the sensing layer, the measured output signal is no longer controlled by the flux of glucose and is no longer linearly proportional to the flux or concentration of glucose. In this case, only a fraction of the glucose arriving at the sensing layer is consumed before the sensor becomes saturated, whereupon the measured signal stops increasing, or increases only slightly, with the concentration of glucose. In a glucose sensor equipped with a diffusion-limiting membrane, on the other hand, the membrane reduces the flux of glucose to the sensing layer such that the sensor does not become saturated and can therefor operate effectively within a much wider range of glucose concentration.

More particularly, in these membrane-equipped glucose sensors, the glucose consumption rate is controlled by the diffusion or flux of glucose through the membrane rather than by the kinetics of the sensing layer. The flux of glucose through the membrane is defined by the permeability of the membrane to glucose, which is usually constant, and by the concentration of glucose in the solution or biofluid being monitored. When all of the glucose arriving at the sensing layer is consumed, the flux of glucose through the membrane to the sensing layer varies linearly with the concentration of glucose in the solution, and determines the measured conversion rate or signal output such that it is also linearly proportional to the concentration of glucose concentration in the solution. Although not necessary, a linear relationship between the output signal and the concentration of glucose in the solution is ideal for the calibration of an implantable sensor.

Implantable amperometric glucose sensors based on the electrooxidation of hydrogen peroxide, as described above, require excess oxygen reactant to ensure that the sensor output is only controlled by the concentration of glucose in the body fluid or tissue being monitored. That is, the sensor is designed to be unaffected by the oxygen typically present in body fluid or tissue. In body tissue in which the glucose sensor is typically implanted, the concentration of oxygen can be very low, such as from about 0.02 mM to about 0.2 mM, while the concentration of glucose can be as high as about 30 mM or, more. Without a glucose-diffusion-limiting membrane, the sensor would become saturated very quickly at very low glucose concentrations. The sensor thus benefits from having a sufficiently oxygen-permeable membrane that restricts glucose flux to the sensing layer, such that the so-called "oxygen-deficiency problem," a condition in which there is insufficient oxygen for adequate sensing to take place, is minimized or eliminated.

In implantable amperometric glucose sensors that employ wired-enzyme electrodes, as described above, there is no oxygen-deficiency problem because oxygen is not a necessary reactant. Nonetheless, these sensors require glucose-diffusion-limiting membranes because typically, for glucose sensors that lack such membranes, the current output reaches a maximum level around or below a glucose concentration of 10 mM, which is well below 30 mM, the high end of clinically relevant glucose concentration.

A diffusion-limiting membrane is also of benefit in a biosensor that employs a wired-enzyme electrode, as the membrane significantly reduces chemical and biochemical reactivity in the sensing layer and thus reduces the production of radical species that can damage the enzyme. The diffusion-limiting membrane may also act as a mechanical protector that prevents the sensor components from leaching out of the sensor layer and reduces motion-associated noise.

There have been various attempts to develop a glucose-diffusion-limiting membrane that is mechanically strong, biocompatible, and easily manufactured. For example, a laminated microporous membrane with mechanical holes has been described (U.S. Pat. No. 4,759,828 of Young et al.) and membranes formed from polyurethane are also known (Shaw, G. W., et al., Biosensors and Bioelectronics 6, 401 (1991); Bindra, D. S., et al., Anal. Chem. 63, 1692 (1991); Shichiri, M., et al., Horm. Metab. Res., Suppl. Ser. 20, 17 (1988)). Supposedly, glucose diffuses through the mechanical holes or cracks in these various membranes. Further by way of example, a heterogeneous membrane with discrete hydrophobic and hydrophilic regions (U.S. Pat. No. 4,484,987 of Gough) and homogenous membranes with both hydrophobic and hydrophilic functionalities (U.S. Pat. Nos. 5,284,140 and 5,322,063 of Allen et al.) have been described. However, all of these known membranes are difficult to manufacture and have inadequate physical properties.

An improved membrane formed from a complex mixture of a diisocyanate, a diol, a diamine and a silicone polymer has been described in U.S. Pat. No. 5,777,060 (Van Antwerp), U.S. Pat. No. 5,786,439 (Van Antwerp et al.) and U.S. Pat. No. 5,882,494 (Van Antwerp). As described therein, the membrane material is simultaneously polymerized and crosslinked in a flask; the resulting polymeric material is dissolved in a strong organic solvent, such as tetrahydroforan (THF); and the resulting solution is applied onto the sensing layer to form the membrane. Unfortunately, a very strong organic solvent, such as THF, can denature the enzyme in the sensing layer and also dissolve conductive ink materials as well as any plastic materials that may be part of the sensor. Further, since the polymerization and crosslinking reactions are completed in the reaction flask, no further bond-making reactions occur when the solution is applied to the sensing layer to form the membrane. As a result, the adhesion between the membrane layer and sensing layer may not be adequate.

In the published Patent Cooperation Treaty (PCT) Application bearing. International Publication No. WO 01/57241 A2, Kelly and Schiffer describe a method for making a glucose-diffusion-limiting membrane by photolytically polymerizing small hydrophilic monomers. The sensitivities of the glucose sensors employing such membranes are widely scattered, however, indicating a lack of control in the membrane-making process. Further, as the polymerization involves very small molecules, it is quite possible that small, soluble molecules remain after polymerization, which may leach out of the sensor. Thus, glucose sensors employing such glucose-diffusion-limiting membranes may not be suitable for implantation in a living body.

SUMMARY OF THE INVENTION

The present invention is directed to membranes composed of crosslinked polymers containing heterocyclic nitrogen groups, particularly polymers of polyvinylpyridine and polyvinylimidazole, and to electrochemical sensors equipped with such membranes. The membranes are useful in limiting the flux of an analyte to a working electrode in an electrochemical sensor so that the sensor is linearly responsive over a large range of analyte concentrations and is easily calibrated. Electrochemical sensors equipped with membranes of the present invention demonstrate considerable sensitivity and stability, and a large signal-to-noise ratio, in a variety of conditions.

According to one aspect of the invention, the membrane is formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer is made from a precursor polymer containing heterocyclic nitrogen groups. Preferably, the precursor polymer is polyvinylpyridine or polyvinylimidazole. When used in an electrochemical sensor, the membrane limits the flux of an analyte reaching a sensing layer of the sensor, such as an enzyme-containing sensing layer of a "wired enzyme" electrode, and further protects the sensing layer. These qualities of the membrane significantly extend the linear detection range and the stability of the sensor.

In the membrane formation process, the non-pyridine copolymer component generally enhances the solubility of the polymer and may provide further desirable physical or chemical properties to the polymer or the resulting membrane. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane. In the formation of a membrane of the present invention, the zwitterionic moiety of the polymer is believed to provide an additional layer of crosslinking, via intermolecular electrostatic bonds, beyond the basic crosslinking generally attributed to covalent bonds, and is thus believed to strengthen the membrane.

Another aspect of the invention concerns the preparation of a substantially homogeneous, analyte-diffusion-limiting membrane that may be used in a biosensor, such as an implantable amperometric biosensor. The membrane is formed in situ by applying an alcohol-buffer solution of a crosslinker and a modified polymer over an enzyme-containing sensing layer and allowing the solution to cure for one to two days. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of the these factors. Amperometric glucose sensors equipped with diffusion-limiting membranes of the present invention demonstrate excellent stability and fast and linear responsivity to glucose concentration over a large glucose concentration range.

BRIEF DESCRIPTION OF THE DRAWINGS

FIG. 2A is a schematic, side-view illustration of a portion of a two-electrode glucose sensor having a working electrode, a combined counter/reference electrode, and a dip-coated membrane that encapsulates both electrodes, according to the present invention. FIGS. 2B and 2C are schematic top- and bottom-view illustrations, respectively, of the portion of the glucose sensor of FIG. 2A. Herein, FIGS. 2A, 2B and 2C may be collectively referred to as FIG. 2.

DESCRIPTION OF THE INVENTION

Figure 1:
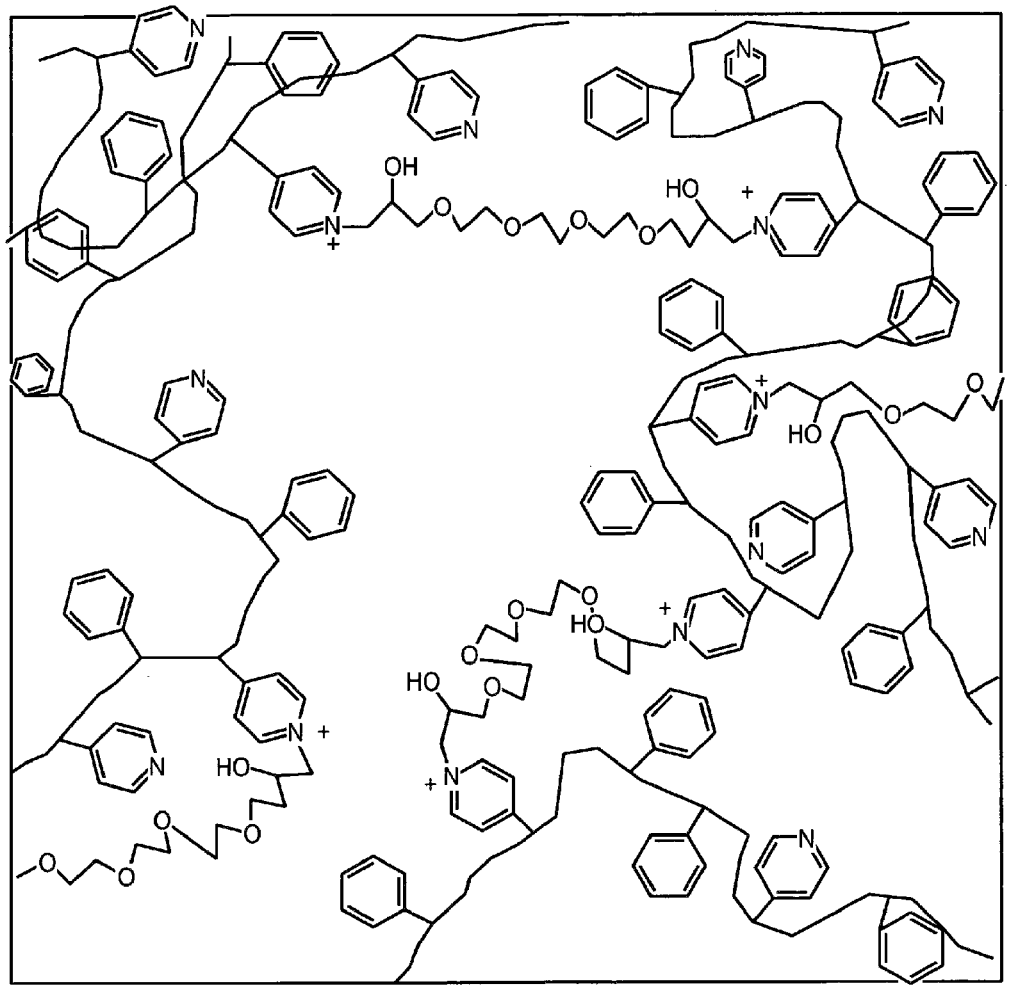
FIG. 1 is an illustration of a typical structure of a section of an analyte-diffusion-limiting membrane, according to the present invention.

When used herein, the terms in quotation marks are defined as set forth below.

The term "alkyl" includes linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

The term "alkoxy" describes an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH2, alkylamino, dialkylamino, trialkylammonium, alkanoylamino, arylcarboxamido, hydrazino, alkylthio, alkenyl, and reactive groups.

A "crosslinker" is a molecule that contains at least two reactive groups capable of linking at least two molecules together, or linking at least two portions of the same molecule together. Linking of at least two molecules is called intermolecular crosslinking, while linking of at least two portions of the same molecule is called intramolecular crosslinking. A crosslinker having more than two reactive groups may be capable of both intermolecular and intramolecular crosslinkings at the same time.

The term "precursor polymer" refers to the starting polymer before the various modifier groups are attached to form a modified polymer.

The term "heterocyclic nitrogen group" refers to a cyclic structure containing a $sp^2$ hybridized nitrogen in a ring of the structure.

The term "polyvinylpyridine" refers to poly(4-vinylpyridine), poly(3-vinylpyridine), or poly(2-vinylpyridine), as well as any copolymer of vinylpyridine and a second or a third copolymer component.

The term "polyvinylimidazole" refers to poly(1-vinylimidazole), poly(2-vinylimidazole), or poly(4-vinylimidazole).

A "membrane solution" is a solution that contains all necessary components for crosslinking and forming the membrane, including a modified polymer containing heterocyclic nitrogen groups, a crosslinker and a buffer or an alcohol-buffer mixed solvent.

A "biological fluid" or "biofluid" is any body fluid or body fluid derivative in which the analyte can be measured, for example, blood, interstitial fluid, plasma, dermal fluid, sweat, and tears.

An "electrochemical sensor" is a device configured to detect the presence of or measure the concentration or amount of an analyte in a sample via electrochemical oxidation or reduction reactions. Typically, these reactions can be transduced to an electrical signal that can be correlated to an amount or concentration of analyte.

A "redox mediator" is an electron-transfer agent for carrying electrons between an analyte, an analyte-reduced or analyte-oxidized enzyme, and an electrode, either directly, or via one or more additional electron-transfer agents. A redox mediator that includes a polymeric backbone may also be referred to as a "redox polymer".

The term "reference electrode" includes both a) reference electrodes and b) reference electrodes that also function as counter electrodes (i.e., counter/reference electrodes), unless otherwise indicated.

The term "counter electrode" includes both a) counter electrodes and b) counter electrodes that also function as reference electrodes (i.e., counter/reference electrodes), unless otherwise indicated.

In general, membrane of the present invention is formed by crosslinking a modified polymer containing heterocyclic nitrogen groups in an alcohol-buffer mixed solvent and allowing the membrane solution to cure over time. The polymer comprises poly(heterocyclic nitrogen-containing constituent) as a portion of its backbone and additional elements, including a zwitterionic moiety, a hydrophobic moiety, and optionally, a biocompatible moiety. The resulting membrane is capable of limiting the flux of an analyte from one space, such as a space associated with a biofluid, to another space, such as space associated with an enzyme-containing sensing layer. An amperometric glucose sensor constructed of a wired-enzyme sensing layer and a glucose-diffusion-limiting layer of the present invention is very stable and has a large linear detection range.

Heterocyclic-Nitrogen Containing Polymers

The polymer of the present invention has the following general formula, Formula 1a:

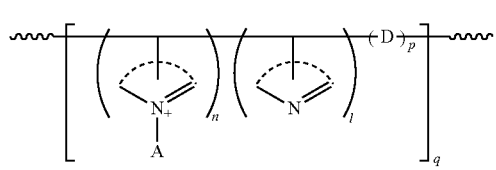

wherein the horizontal line represents a polymer backbone; A is an alkyl group substituted with a water soluble group, preferably a negatively charged group, such as sulfonate, phosphate, or carboxylate, and more preferably, a strong acid group such as sulfonate, so that the quaternized heterocyclic nitrogen to which it is attached is zwitterionic; D is a copolymer component of the polymer, as further described below; each of n, l, and p is independently an average number of an associated polymer unit or polymer units shown in the closest parentheses to the left; and q is a number of a polymer unit or polymer units shown in the brackets.

The heterocyclic nitrogen groups of Formula 1a include, but are not limited to, pyridine, imidazole, oxazole, thiazole, pyrazole, or any derivative thereof. Preferably, the heterocyclic nitrogen groups are independently vinylpyridine, such as 2-, 3-, or 4-vinylpyridine, or vinylimidazole, such as 1-, 2-, or 4-vinylimidazole. More preferably, the heterocyclic nitrogen groups are independently 4-vinylpyridine, such that the more preferable polymer is a derivative of poly(4-vinylpyridine). An example of such a poly(4-vinylpyridine) of the present invention has the following general formula, Formula 1b:

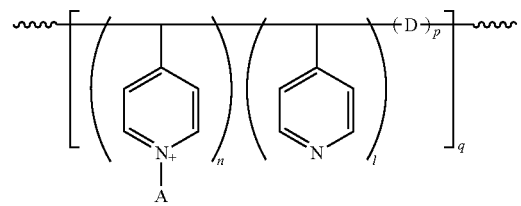

wherein A, D, n, l, p and q are as described above in relation to Formula 1a.

While the polymer of the present invention has the general Formula 1a or Formula 1b above, it should be noted that when A is a strong acid, such as a stronger acid than carboxylic acid, the D component is optional, such that p may equal zero. Such a polymer of the present invention has the following general formula, Formula 1c:

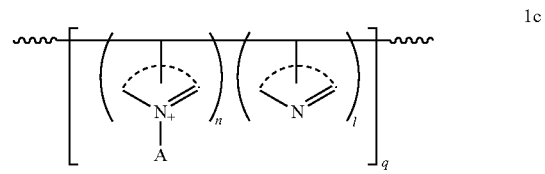

wherein A is a strong acid and the heterocyclic nitrogen groups, n, l and q are all as described above. Sulfonate and fluorinated carboxylic acid are examples of suitably strong acids. It is believed that when A is a sufficiently strong acid, the heterocyclic nitrogen to which it is attached becomes zwitterionic and thus capable of forming intermolecular electrostatic bonds with the crosslinker during membrane formation. It is believed that these intermolecular electrostatic bonds provide another level of crosslinking, beyond the covalent bonds typical of crosslinking, and thus make the resulting membrane stronger. As a result, when A is a suitably strong acid, the D component, which is often a strengthening component such as styrene, may be omitted from the polymers of Formulas 1a and 1b above. When A is a weaker acid, such that the heterocyclic nitrogen is not zwitterionic or capable of forming intermolecular electrostatic bonds, the polymer of the present invention does include D, as shown in Formulas 1a and 1b above.

Examples of A include, but are not limited to, sulfopropyl, sulfobutyl, carboxypropyl, and carboxypentyl. In one embodiment of the invention, group A has the formula -L-G, where L is a C2-C12 linear or branched alkyl linker optionally and independently substituted with an aryl, alkoxy, alkenyl, alkynyl, —F, —Cl, —OH, aldehyde, ketone, ester, or amide group, and G is a negatively charged carboxy or sulfonate group. The alkyl portion of the substituents of L have 1-6 carbons and are preferably an aryl, —OH or amide group.

A can be attached to the heterocyclic nitrogen group via quaternization with an alkylating agent that contains a suitable linker L and a negatively charged group G, or a precursor group that can be converted to a negatively charged group G at a later stage. Examples of suitable alkylating agents include, but are not limited to, 2-bromoethanesulfonate, propanesultone, butanesultone, bromoacetic acid, 4-bromobutyric acid and 6-bromohexanoic acid. Examples of alkylating agents containing a precursor group include, but are not limited to, ethyl bromoacetate and methyl 6-bromohexanoate. The ethyl and methyl ester groups of these precursors can be readily converted to a negatively charged carboxy group by standard hydrolysis.

Alternatively, A can be attached to the heterocyclic nitrogen group by quaternizing the nitrogen with an alkylating agent that contains an additional reactive group, and subsequently coupling, via standard methods, this additional reactive group to another molecule that contains a negatively charged group G and a reactive group. Typically, one of the reactive groups is an electrophile and the other reactive group is a nucleophile. Selected examples of reactive groups and the linkages formed from their interactions are shown in Table 1.

TABLE 1

Examples of Reactive Groups and Resulting Linkages

| First Reactive Group | Second Reactive Group | Resulting Linkage |
|---|---|---|
| Activated ester* | Amine | Amide |
| Acrylamide | Thiol | Thioether |
| Acyl azide | Amine | Amide |
| Acyl halide | Amine | Amide |
| Carboxylic acid | Amine | Amide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Ester |
| Alkyl halide | Imidazole | Imidazolium |
| Alkyl halide | Pyridine | Pyridinium |
| Alkyl halide | Alcohol/phenol | Ether |
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Amide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing group such as sulfo, nitro, cyano, or halo; or carboxylic acids activated by carbodiimides.

By way of example, A may be attached to the heterocyclic nitrogen groups of the polymer by quaternizing the heterocyclic nitrogens with 6-bromohexanoic acid and subsequently coupling the carboxy group to the amine group of 3-amino-1-propanesulfonic acid in the presence of a carbodiimide coupling agent.

D is a component of a poly(heterocyclic nitrogen-co-D) polymer of Formula 1a or 1b. Examples of D include, but are not limited to, phenylalkyl, alkoxystyrene, hydroxyalkyl, alkoxyalkyl, alkoxycarbonylalkyl, and a molecule containing a poly(ethylene glycol) or polyhydroxyl group. Some poly(heterocyclic nitrogen-co-D) polymers suitable as starting materials for the present invention are commercially available. For example, poly(2-vinylpyridine-co-styrene), poly(4-vinylpyridine-co-styrene) and poly(4-vinylpyridine-co-butyl methacrylate) are available from Aldrich Chemical Company, Inc. Other poly(heterocyclic nitrogen-co-D) polymers can be readily synthesized by anyone skilled in the art of polymer chemistry using well-known methods. Preferably, D is a styrene or a C1-C18 alkyl methacrylate component of a polyvinylpyridine-poly-D, such as (4-vinylpyrine-co-styrene) or poly(4-vinylpyridine-co-butyl methacrylate), more preferably, the former. D may contribute to various desirable properties of the membrane including, but not limited to, hydrophobicity, hydrophilicity, solubility, biocompatibility, elasticity and strength. D may be selected to optimize or "fine-tune" a membrane made from the polymer in terms of its permeability to an analyte and its non-permeability to an undesirable, interfering component, for example.

The letters n, l, and p designate, respectively, an average number of each copolymer component in each polymer unit. The letter q is one for a block copolymer or a number greater than one for a copolymer with a number of repeating polymer units. By way of example, the q value for a polymer of the present invention may be ≥about 950, where n, l and p are 1, 8 and 1, respectively. The letter q is thus related to the overall molecular weight of the polymer. Preferably, the average molecular weight of the polymer is above about 50,000, more preferably above about 200,000, most preferably above about 1,000,000.

The polymer of the present invention may comprise a further, optional copolymer, as shown in the following general formula, Formula 2a:

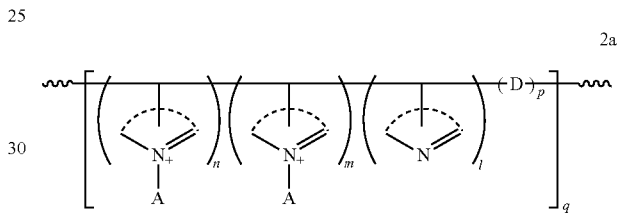

2a wherein the polymer backbone, A, D, n, l, p and q are as described above in relation to Formulas 1a-1c; m is an average number of an associated polymer unit or polymer units shown in the closest parentheses to the left; and B is a modifier. When the heterocyclic nitrogen groups are 4-substituted pyridine, as is preferred, the polymer of the present invention is derivative of poly(4-vinylpyridine) and has the general formula, Formula 2b, set forth below.

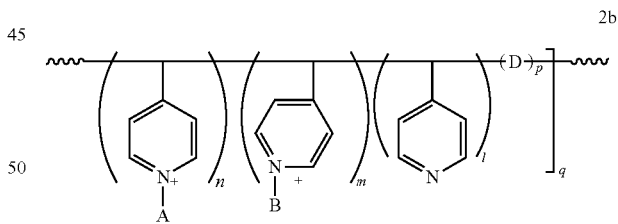

2b

Further, when A is a suitably strong acid, as described above, the D copolymer is optional, in which case the polymer of the present invention has the general formula, Formula 2c:

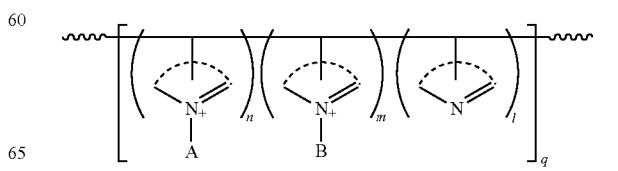

2c

In any of Formulas 2a-2c, B is a modifier group that may add any desired chemical, physical or biological properties to the membrane. Such desired properties include analyte selectivity, hydrophobicity, hydrophilicity, elasticity, and biocompatibility. Examples of modifiers include the following: negatively charged molecules that may minimize entrance of negatively charged, interfering chemicals into the membrane; hydrophobic hydrocarbon molecules that may increase adhesion between the membrane and sensor substrate material; hydrophilic hydroxyl or polyhydroxy molecules that may help hydrate and add biocompatibility to the membrane; silicon polymers that may add elasticity and other properties to the membrane; and poly(ethylene glycol) constituents that are known to increase biocompatibility of biomaterials (Bergstrom, K., et al., J. Biomed. Mat. Res. 26, 779 (1992)). Further examples of B include, but are not limited to, a metal chelator, such as a calcium chelator, and other biocompatible materials. A poly(ethylene glycol) suitable for biocompatibility modification of the membrane generally has a molecular weight of from about 100 to about 20,000, preferably, from about 500 to about 10,000, and more preferably, from about 1,000 to about 8,000.

The modifier B can be attached to the heterocyclic nitrogens of the polymer directly or indirectly. In direct attachment, the heterocyclic nitrogen groups may be reacted with a modifier containing an alkylating group. Suitable alkylating groups include, but are not limited to, alkyl halide, epoxide, aziridine, and sulfonate esters. In indirect attachment, the heterocyclic nigrogens of the polymer may be quaternized with an alkylating agent having an additional reactive group, and then attached to a molecule having a desired property and a suitable reactive group.

As described above, the B-containing copolymer is optional in the membrane of the present invention, such that when m of Formula 2a-2c is zero, the membrane has the general formula of Formula 1a-1c, respectively. The relative amounts of the four copolymer components, the heterocyclic nitrogen group containing A, the optional heterocyclic nitrogen group containing B, the heterocyclic nitrogen group, and D, may be expressed as percentages, as follows: [n/(n+m+l+p)]×100%, [m/(n+m+l+p)]×100%, [l/(n+m+l+p)]×100%, and [p/(n+m+l+p)]×100%, respectively. Suitable percentages are 1-25%, 0-15% (when the B-containing heterocyclic nitrogen group is optional) or 1-15%, 20-90%, and 0-50% (when D is optional) or 1-50%, respectively, and preferable percentages are 5-20%, 0-10% (when the B-containing heterocyclic nitrogen group is optional) or 1-10%, 60-90%, and 5-20%, respectively.

Specific examples of suitable polymers have the general formulas, Formulas 3-6, shown below.

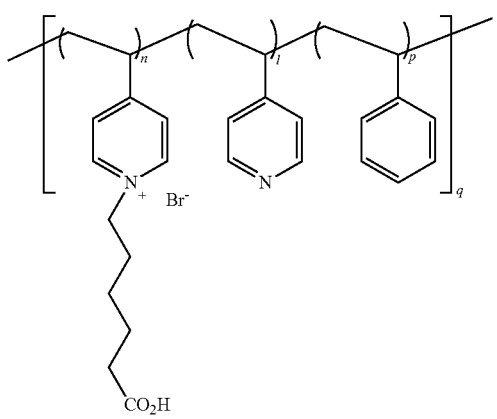

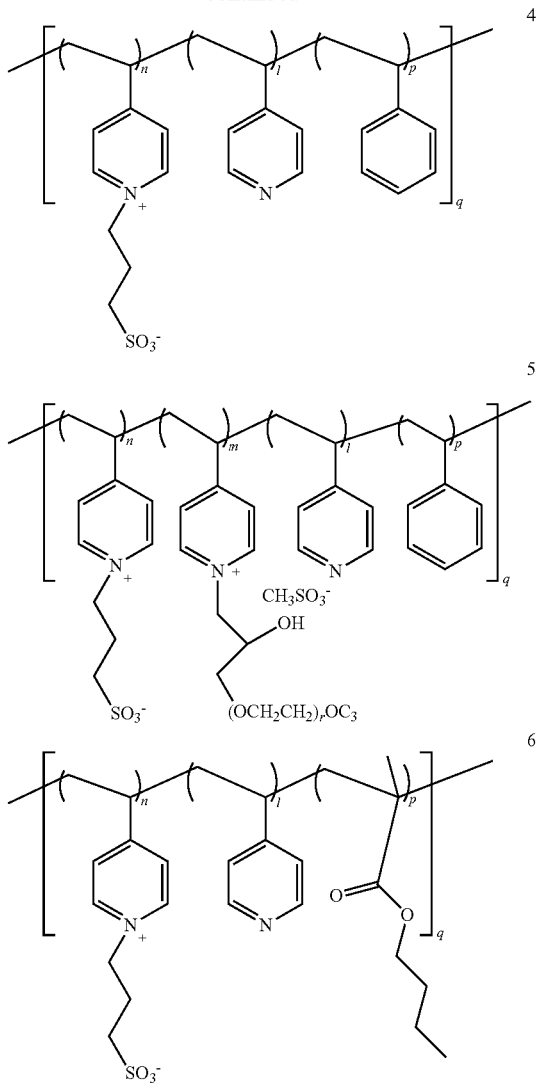

EXAMPLES OF SYNTHESES OF POLYVINYLPYRIDINE POLYMERS

Examples showing the syntheses of various polyvinylpyridine polymers according to the present invention are provided below. Numerical figures provided are approximate.

Example 1

Synthesis of a Polymer of Formula 3

By way of illustration, an example of the synthesis of a polymer of Formula 3 above, is now provided. A solution of poly(4-vinylpyridine-co-styrene) (~10% styrene content) (20 g, Aldrich) in 100 mL of dimethyl formamide (DMF) at 90° C. was stirred and 6-bromohexanoic acid (3.7 g) in 15-20 mL of DMF was added. The resulting solution was stirred at 90° C. for 24 hours and then poured into 1.5 L of ether, whereupon the solvent was decanted. The remaining, gummy solid was dissolved in MeOH (150-200 mL) and suction-filtered through a medium-pore, fitted funnel to remove any undissolved solid. The filtrate was added slowly to rapidly stirred ether (1.5 L) in a beaker. The resulting precipitate was collected by suction filtration and dried at 50° C. under high vacuum for 2 days. The polymer had the following parameters: $[n/(n+l+p)] \times 100\% \approx 10\%$; $[l/(n+l+p)] \times 100\% \approx 80\%$; and $[p/(n+l+p)] \times 100\%$

Example 2

Synthesis of a Polymer of Formula 5

By way of illustration, an example of the synthesis of a polymer of Formula 5 above, is now provided. A solution of poly(4-vinylpyridine-co-styrene) (~10% styrene) (20 g, Aldrich) in 100 mL of anhydrous DMF at 90° C. was stirred, methanesulfonic acid (~80 mg) was added, and then 2 g of methoxy-PEG-epoxide (molecular weight 5,000) (Shearwater Polymers, Inc.) in 15-20 mL of anhydrous DMF was added. The solution was stirred at 90° C. for 24 hours and 1,3-Propane sultone (2.32 g) in 10 mL of anhydrous DMF was added. The resulting solution was continuously stirred at 90° for 24 hours, and then cooled to room temperature and poured into 800 mL of ether. The solvent was decanted and the remaining precipitate was dissolved in hot MeOH (~200 mL), suction-filtered, precipitated again from 1 L of ether, and then dried at 50° C. under high vacuum for 48 hours. The resulting polymer has the following parameters: $[n/(n+m+l+p)] \times 100\% \approx 10\%$; $[m/(n+m+l+p)] \times 100\% \approx 10\%$; $[l/(n+m+l+p)] \times 100\% \approx 70\%$; and $[p/(n+m+l+p)] \times 100\%$

Example 3

Synthesis of a Polymer Having a Polyhydroxy Modifier B

By way of illustration, an example of the synthesis of a polymer having a polyhydroxy modifier B, as schematically illustrated below, is now provided. Various polyhydroxy compounds are known for having biocompatibility properties. (U.S. Pat. No. 6,011,077.) The synthesis below illustrates how a modifier group having a desired property may be attached to the polymer backbone via a linker.

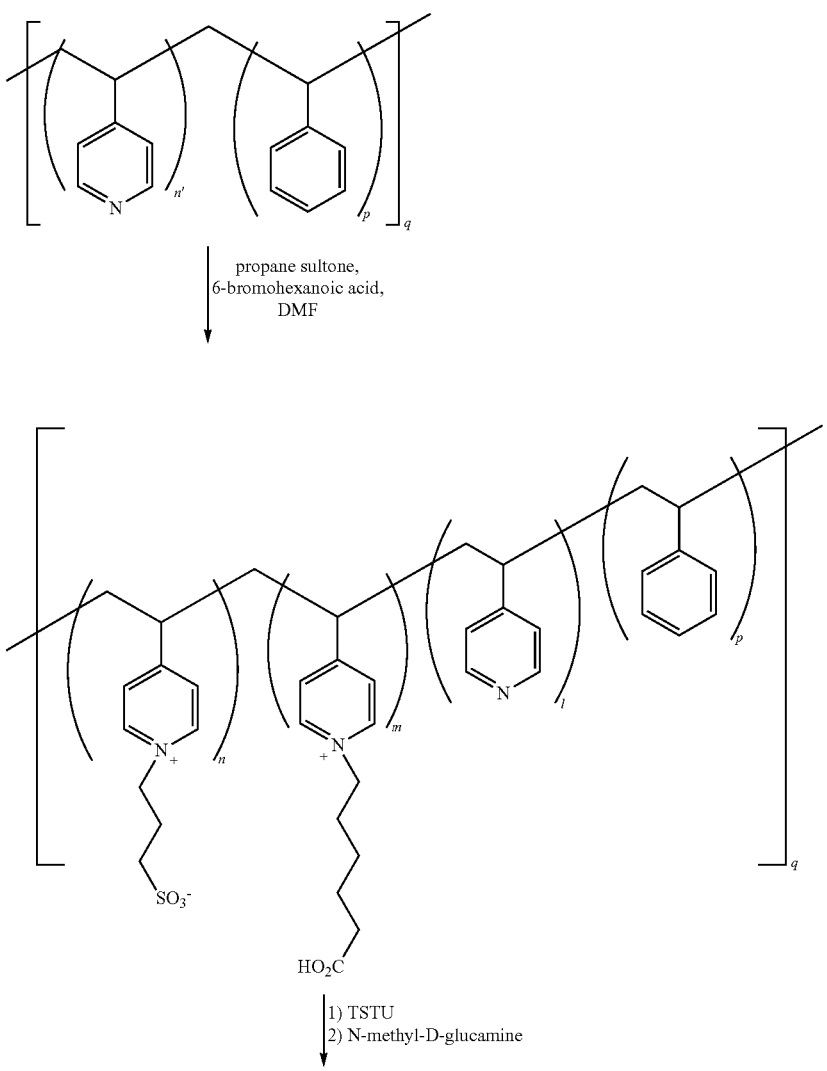

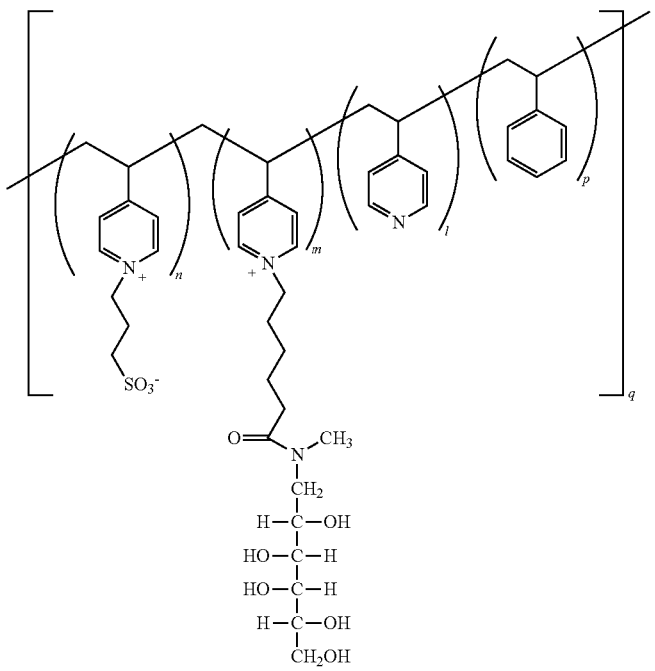

1,3-propane sultone (0.58 g, 4.8 mmoles) and 6-bromohexanoic acid (1.85 g, 9.5 mmoles) are added to a solution of poly(4-vinylpyridine-co-styrene) (~10% styrene) (10 g) dissolved in 60 mL of anhydrous DMF. The resulting solution is stirred at 90° C. for 24 hours and then cooled to room temperature. O—(N-succinimidyl)-N,N,N',N'-tetramethyl-uronium tetrafluoroborate (TSTU) (2.86 g, 9.5 mmoles) and N,N-diisopropylethylamine (1.65 mL, 9.5 mmoles) are then added in succession to the solution. After the solution is stirred for 5 hours, N-methyl-D-glucamine (2.4 g, 12.4 mmoles) is added and the resulting solution is stirred at room temperature for 24 hours. The solution is poured into 500 ml of ether and the precipitate is collected by suction filtration. The collected precipitate is then dissolved in MeOH/H$_2$O and the resulting solution is subjected to ultra membrane filtration using the same MeOH/H$_2$O solvent to remove small molecules. The dialyzed solution is evaporated to dryness to give a polymer with the following parameters: [n/(n+m+l+p)]×100%≈10%; [m/(n+m+l+p)]×100%≈10%; [l/(n+m+l+p)]×100%≈70%; and [p/(n+m+l+p)]×100%≈10%.

Crosslinkers

Crosslinkers of the present invention are molecules having at least two reactive groups, such as bi-, tri-, or tetra-functional groups, capable of reacting with the heterocyclic nitrogen groups, pyridine groups, or other reactive groups contained on A, B or D of the polymer. Preferably, the reactive groups of the crosslinkers are slow-reacting alkylating groups that can quaternize the heterocyclic nitrogen groups, such as pyridine groups, of the polymer. Suitable alkylating groups include, but are not limited to, derivatives of poly(ethylene glycol) or poly(propylene glycol), epoxide (glycidyl group), aziridine, alkyl halide, and sulfonate esters. Alkylating groups of the crosslinkers are preferably glycidyl groups. Preferably, glycidyl crosslinkers have a molecular weight of from about 200 to about 2,000 and are water soluble or soluble in a water-miscible solvent, such as an alcohol. Examples of suitable crosslinkers include, but are not limited to, poly(ethylene glycol) diglycidyl ether with a molecular weight of about 200 to about 600, and N,N-diglycidyl-4-glycidyloxyaniline.

It is desirable to have a slow crosslinking reaction during the dispensing of membrane solution so that the membrane coating solution has a reasonable pot-life for large-scale manufacture. A fast crosslinking reaction results in a coating solution of rapidly changing viscosity, which renders coating difficult. Ideally, the crosslinking reaction is slow during the dispensing of the membrane solution, and accelerated during the curing of the membrane at ambient temperature, or at an elevated temperature where possible.

Membrane Formation and Sensor Fabrication

An example of a process for producing a membrane of the present invention is now described. In this example, the polymer of the present invention and a suitable crosslinker are dissolved in a buffer-containing solvent, typically a buffer-alcohol mixed solvent, to produce a membrane solution. Preferably, the buffer has a pH of about 7.5 to about 9.5 and the alcohol is ethanol. More preferably, the buffer is a 10 mM (2-(4-(2-hydroxyethyl)-1-piperazine)ethanesulfonate) (HEPES) buffer (pH 8) and the ethanol to buffer volume ratio is from about 95 to 5 to about 0 to 100. A minimum amount of buffer is necessary for the crosslinking chemistry, especially if an epoxide or aziridine crosslinker is used. The amount of solvent needed to dissolve the polymer and the crosslinker may vary depending on the nature of the polymer and the crosslinker. For example, a higher percentage of alcohol may be required to dissolve a relatively hydrophobic polymer and/or crosslinker.

The ratio of polymer to cross-linker is important to the nature of the final membrane. By way of example, if an inadequate amount of crosslinker or an extremely large excess of crosslinker is used, crosslinking is insufficient and the membrane is weak. Further, if a more than adequate amount of crosslinker is used, the membrane is overly crosslinked such that membrane is too brittle and/or impedes analyte diffusion. Thus, there is an optimal ratio of a given polymer to a given crosslinker that should be used to prepare a desirable or useful membrane. By way of example, the optimal polymer to crosslinker ratio by weight is typically from about 4:1 to about 32:1 for a polymer of any of Formulas 3-6 above and a poly(ethylene glycol) diglycidyl ether crosslinker, having a molecular weight of about 200 to about 400. Most preferably, this range is from about 8:1 to about 16:1. Further by way of example, the optimal polymer to crosslinker ratio by weight is typically about 16:1 for a polymer of Formula 4 above, wherein [n/(n+l+p)]×100%≈10%, [l/(n+l+p)]×100%≈80%, and [p/(n+l+p)]×100%≈10%, or for a polymer of Formula 5 above, wherein [n/(n+m+l+p)]×100%≈10%, [m/(n+m+l+p)]×100%≈10%, [l/(n+m+l+p)]×100%≈70%, [p/(n+m+l+p)]×100%≈10%, and r≈110, and a poly(ethylene glycol) diglycidyl ether crosslinker having a molecular weight of about 200.

The membrane solution can be coated over a variety of biosensors that may benefit from having a membrane disposed over the enzyme-containing sensing layer. Examples of such biosensors include, but are not limited to, glucose sensors and lactate sensors. (See U.S. Pat. No. 6,134,461 to Heller et al., which is incorporated herein in its entirety by this reference.) The coating process may comprise any commonly used technique, such as spin-coating, dip-coating, or dispensing droplets of the membrane solution over the sensing layers, and the like, followed by curing under ambient conditions typically for 1 to 2 days. The particular details of the coating process (such as dip duration, dip frequency, number of dips, or the like) may vary depending on the nature (i.e., viscosity, concentration, composition, or the like) of the polymer, the crosslinker, the membrane solution, the solvent, and the buffer, for example. Conventional equipment may be used for the coating process, such as a DSG D1L-160 dip-coating or casting system of NIMA Technology in the United Kingdom.

Example of Sensor Fabrication

Sensor fabrication typically consists of depositing an enzyme-containing sensing layer over a working electrode and casting the diffusion-limiting membrane layer over the sensing layer, and optionally, but preferably, also over the counter and reference electrodes. The procedure below concerns the fabrication of a two-electrode sensor, such as that depicted in FIGS. 2A-2C. Sensors having other configurations such as a three-electrode design can be prepared using similar methods.

A particular example of sensor fabrication, wherein the numerical figures are approximate, is now provided. A sensing layer solution was prepared from a 7.5 mM HEPES solution (0.5 µL, pH 8), containing 1.7 µg of the polymeric osmium mediator compound L, as disclosed in Published Patent Cooperation Treaty (PCT) Application, International Publication No. WO 01/36660 A2, which is incorporated herein in its entirety by this reference; 2.1 µg of glucose oxidase (Toyobo); and 1.3 µg of poly(ethylene glycol) diglycidyl ether (molecular weight 400). Compound L is shown below.

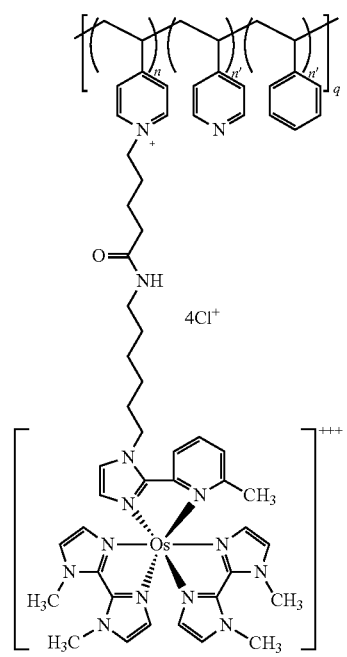

The sensing layer solution was deposited over carbon-ink working electrodes and cured at room temperature for two days to produce a number of sensors. A membrane solution was prepared by mixing 4 volumes of a polymer of Formula 4 above, dissolved at 64 mg/mL in 80% EtOH/20% HEPES buffer (10 mM, pH 8), and one volume of poly(ethylene glycol) diglycidyl ether (molecular weight 200), dissolved at 4 mg/mL in 80% EtOH/20% HEPES buffer (10 mM, pH 8). The above-described sensors were dipped three times into the membrane solution, at about 5 seconds per dipping, with about a 10-minute time interval between consecutive dippings. The sensors were then cured at room temperature and normal humidity for 24 hours.

An approximate chemical structure of a section of a typical membrane prepared according to the present invention is shown in FIG. 1. Such a membrane may be employed in a variety of sensors, such as the two- or three-electrode sensors described previously herein. By way of example, the membrane may be used in a two-electrode amperometric glucose sensor, as shown in FIG. 2A-2C (collectively FIG. 2) and described below.

The amperometric glucose sensor 10 of FIG. 2 comprises a substrate 12 disposed between a working electrode 14 that is typically carbon-based, and a Ag/AgCl counter/reference electrode 16. A sensor or sensing layer 18 is disposed on the working electrode. A membrane or membrane layer 20 encapsulates the entire glucose sensor 10, including the Ag/AgCl counter/reference electrode.

The sensing layer 18 of the glucose sensor 10 consists of crosslinked glucose oxidase and a low potential polymeric osmium complex mediator, as disclosed in the above-mentioned Published PCT Application, International Publication No. WO 01/36660 A2. The enzyme- and mediator-containing formulation that can be used in the sensing layer, and methods for applying them to an electrode system, are known in the art, for example, from U.S. Pat. No. 6,134,461. According to the present invention, the membrane overcoat was formed by thrice dipping the sensor into a membrane solution comprising 4 mg/mL poly(ethylene glycol) diglycidyl ether (molecular weight of about 200) and 64 mg/mL of a polymer of Formula 4 above, wherein $[n/(n+l+p)]\times 100\% \approx 10\%$; $[l/(n+l+p)]\times 100\% \approx 80\%$; and $[p/(n+l+p)]\times 100\% \approx 40\%$, and curing the thrice-dipped sensor at ambient temperature and normal humidity for at least 24 hours, such as for about 1 to 2 days. The q value for such a membrane overcoat may be ≥about 950, where n, l and p are 1, 8 and 1, respectively.

Membrane Surface Modification

Polymers of the present invention have a large number of heterocyclic nitrogen groups, such as pyridine groups, only a few percent of which are used in crosslinking during membrane formation. The membrane thus has an excess of these groups present both within the membrane matrix and on the membrane surface. Optionally, the membrane can be further modified by placing another layer of material over the heterocyclic-nitrogen-group-rich or pyridine-rich membrane surface. For example, the membrane surface may be modified by adding a layer of poly(ethylene glycol) for enhanced biocompatibility. In general, modification may consist of coating the membrane surface with a modifying solution, such as a solution comprising desired molecules having an alkylating reactive group, and then washing the coating solution with a suitable solvent to remove excess molecules. This modification should result in a monolayer of desired molecules.

The membrane 20 of the glucose sensor 10 shown in FIG. 2 may be modified in the manner described above.

Experimental Examples

Examples of experiments that demonstrate the properties and/or the efficacy of sensors having diffusion-limiting membranes according to the present invention are provided below. Numerical figures provided are approximate.

Calibration Experiment

Figure 3:
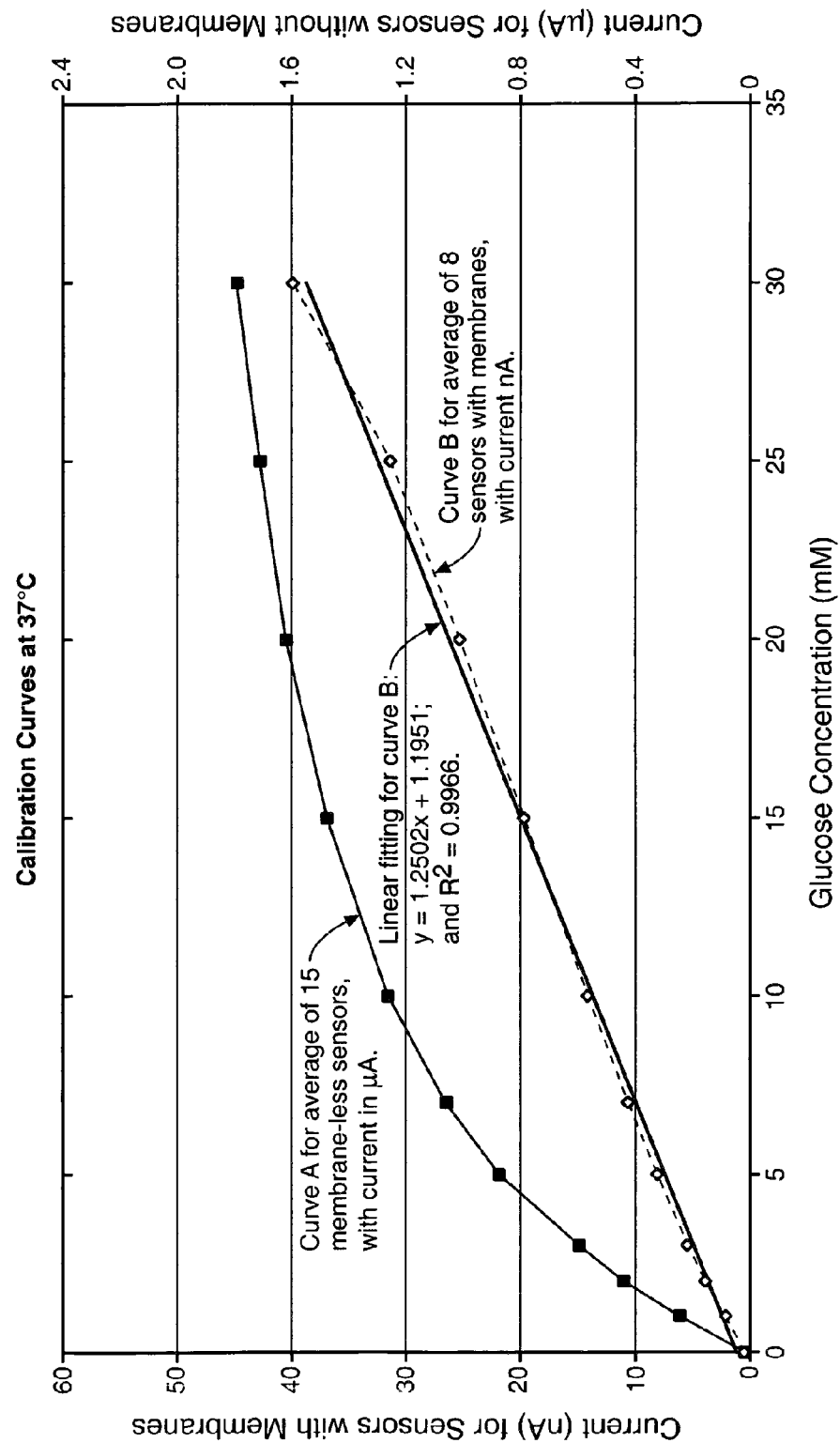
FIG. 3 is a graph of current versus glucose concentration for sensors having glucose-diffusion-limiting membranes, according to the present invention, and for sensors lacking such membranes, based on average values.

In a first example, a calibration experiment was conducted in which fifteen sensors lacking membranes were tested simultaneously (Set 1), and separately, eight sensors having diffusion-limiting membranes according to the present invention were tested simultaneously (Set 2), all at 37° C. In Set 2, the membranes were prepared from polymers of Formula 4 above and poly(ethylene glycol) diglycidyl ether (PEGDGE) crosslinkers, having a molecular weight of about 200. In the calibration experiment for each of Set 1 and Set 2, the sensors were placed in a PBS-buffered solution (pH 7) and the output current of each of the sensors was measured as the glucose concentration was increased. The measured output currents (μA for Set 1; nA for Set 2) were then averaged for each of Set 1 and Set 2 and plotted against glucose concentration (mM), as shown in the calibration graph of FIG. 3.

As shown, the calibration curve for the Set 1 sensors lacking membranes is approximately linear over a very small range of glucose concentrations, from zero to about 3 mM, or 5 mM at most. This result indicates that the membrane-free sensors are insufficiently sensitive to glucose concentration change at elevated glucose concentrations such as 10 mM, which is well below the high end of clinically relevant glucose concentration at about 30 mM. By contrast, the calibration curve for the Set 2 sensors having diffusion-limiting membranes according to the present invention is substantially linear over a relatively large range of glucose concentrations, for example, from zero to about 30 mM, as demonstrated by the best-fit line ($y=1.2502x+1.1951$; $R^2 \approx 0.997$) also shown in FIG. 3. This result demonstrates the considerable sensitivity of the membrane-equipped membranes to glucose concentration, at low, medium, and high glucose concentrations, and of particular relevance, at the high end of clinically relevant glucose concentration at about 30 mM.

Stability Experiment

Figure 4:
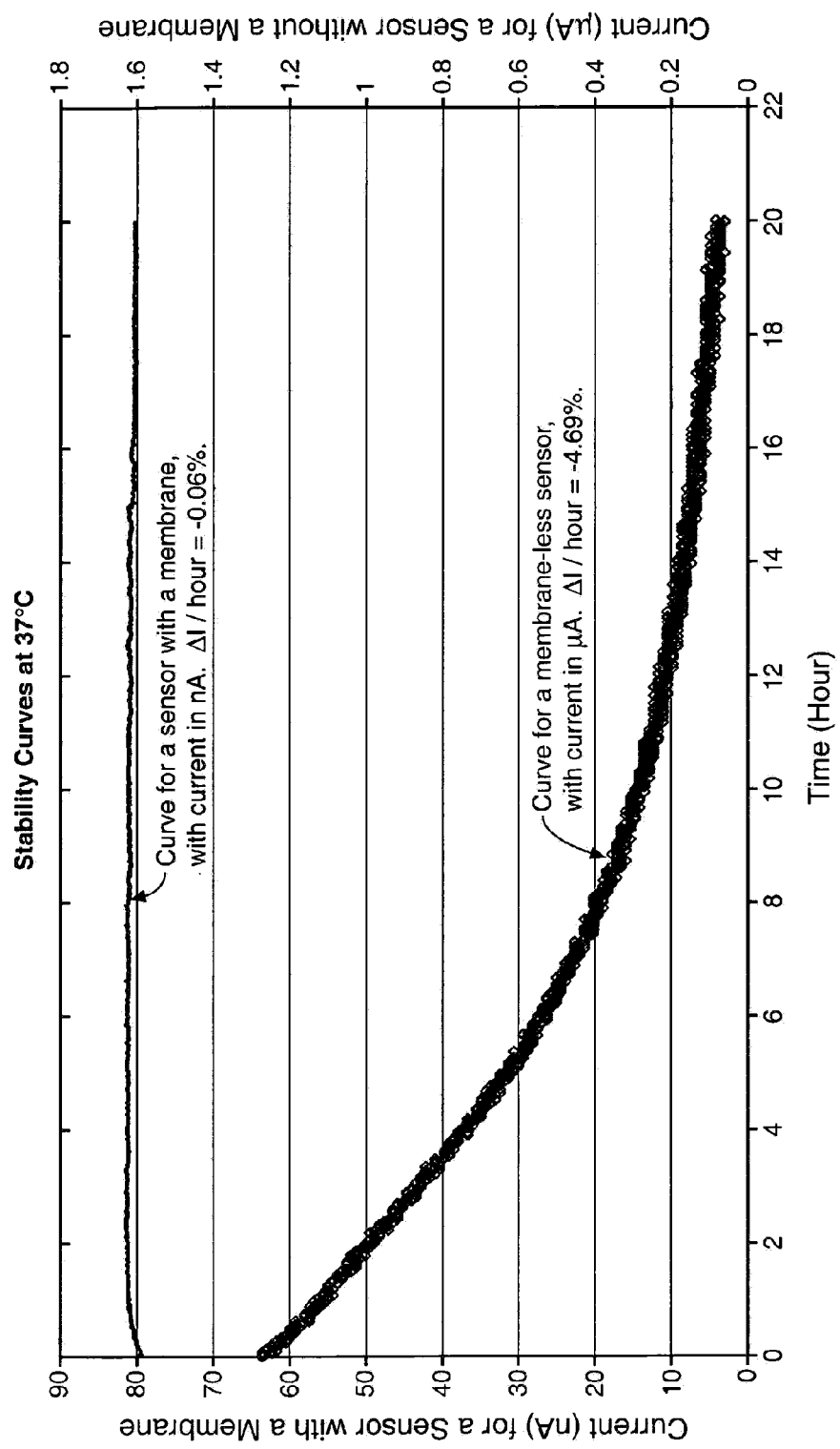
FIG. 4 is a graph of current output versus time at fixed glucose concentration for a sensor having a glucose-diffusion-limiting membrane, according to the present invention, and for a sensor lacking such a membrane.

In a second example, a stability experiment was conducted in which a sensor lacking a membrane and a sensor having a diffusion-limiting membrane according to the present invention were tested, simultaneously, at 37° C. The membrane-equipped sensor had a membrane prepared from the same polymer and the same crosslinker as those of the sensors of Set 2 described above in the calibration experiment. In this stability experiment, each of the sensors was placed in a PBS-buffered solution (pH 7) having a fixed glucose concentration of 30 mM, and the output current of each of the sensors was measured. The measured output currents (μA for the membrane-less sensor; nA for the membrane-equipped sensor) were plotted against time (hour), as shown in the stability graph of FIG. 4.

As shown, the stability curve for the membrane-less sensor decays rapidly over time, at a decay rate of about 4.69% μA per hour. This result indicates a lack of stability in the membrane-less sensor. By contrast, the stability curve for the membrane-equipped sensor according to the present invention shows relative constancy over time, or no appreciable decay over time, the decay rate being only about 0.06% nA per hour. This result demonstrates the considerable stability and reliability of the membrane-equipped sensors of the present invention. That is, at a glucose concentration of 30 mM, while the membrane-less sensor lost sensitivity at a rate of almost 5% per hour over a period of about 20 hours, the membrane-equipped sensor according to the present invention showed virtually no loss of sensitivity over the same period.

Responsivity Experiment

Ideally, the membrane of an electrochemical sensor should not impede communication between the sensing layer of the sensor and fluid or biofluid containing the analyte of interest. That is, the membrane should respond rapidly to changes in analyte concentration.

Figure 5:
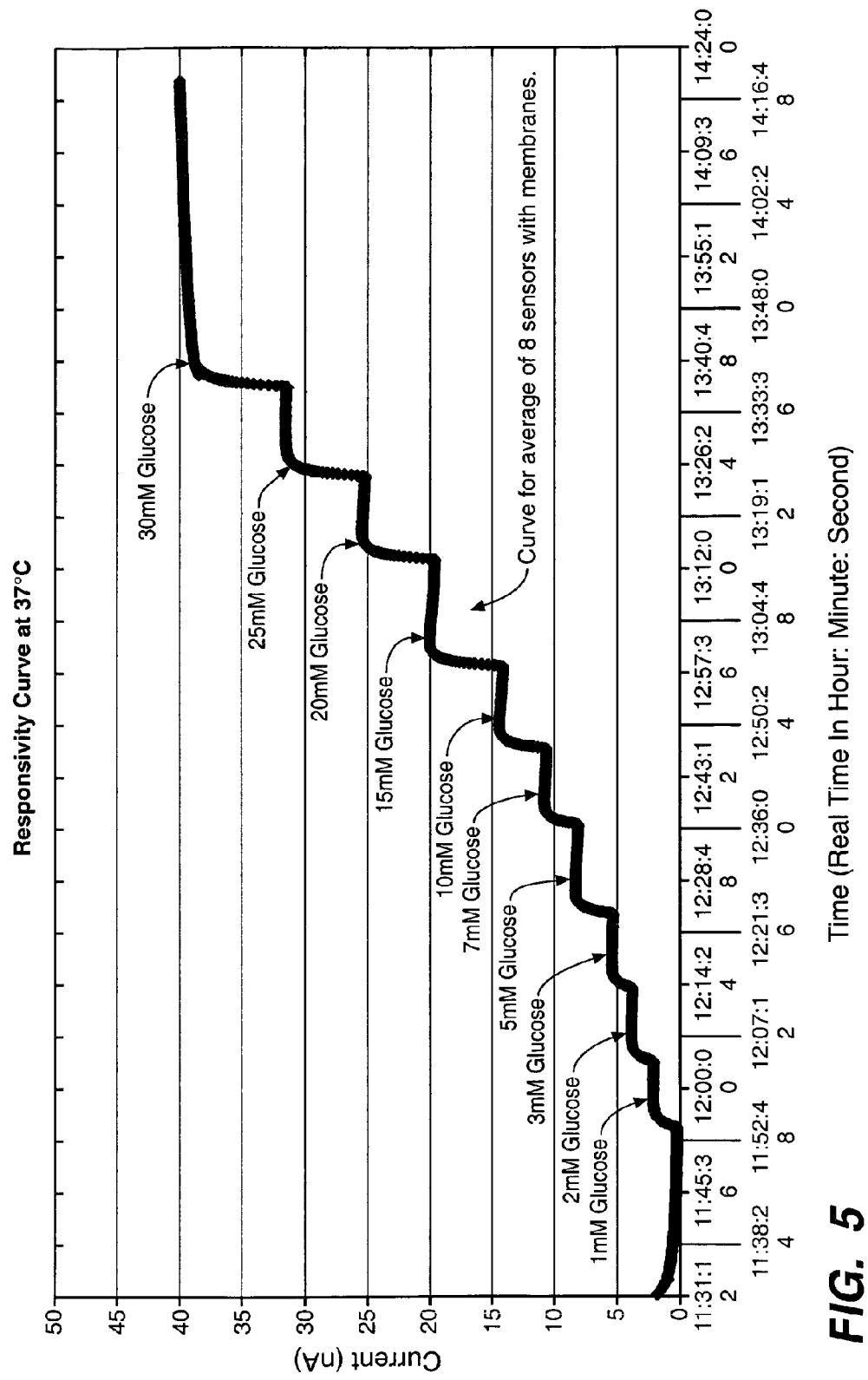
FIG. 5 is a graph of current output versus time at different levels of glucose concentration for sensors having glucose-diffusion-limiting membranes, according to the present invention, based on average values.

In a third example, a responsivity experiment was conducted in which eight sensors having diffusion-limiting membranes according to the present invention were tested simultaneously (Set 3), all at 37° C. The sensors of Set 3 had membranes prepared from the same polymers and the same crosslinkers as those of the sensors of Set 2 described in the calibration experiment above. In this responsivity experiment, the eight sensors were placed in a PBS-buffered solution (pH 7), the glucose concentration of which was increased in a step-wise manner over time, as illustrated by the glucose concentrations shown in FIG. 5, and the output current of each of the sensors was measured. The measured output currents (nA) were then averaged for Set 3 and plotted against time (real time, hour:minute:second), as shown in the responsivity graph of FIG. 5.

The responsivity curve for the Set 3 sensors having diffusion-limiting membranes according to the present invention has discrete steps that mimic the step-wise increases in glucose concentration in a rapid fashion. As shown, the output current jumps rapidly from one plateau to the next after the glucose concentration is increased. This result demonstrates the considerable responsivity of the membrane-equipped sensors of the present invention. The responsivity of these membrane-equipped electrochemical sensors makes them ideal for analyte sensing, such as glucose sensing.

Motion-Sensitivity Experiment

Ideally, the membrane of an electrochemical sensor should be unaffected by motion or movement of fluid or biofluid containing the analyte of interest. This is particularly important for a sensor that is implanted in a body, such as a human body, as body movement may cause motion-associated noise and may well be quite frequent.

Figure 6:
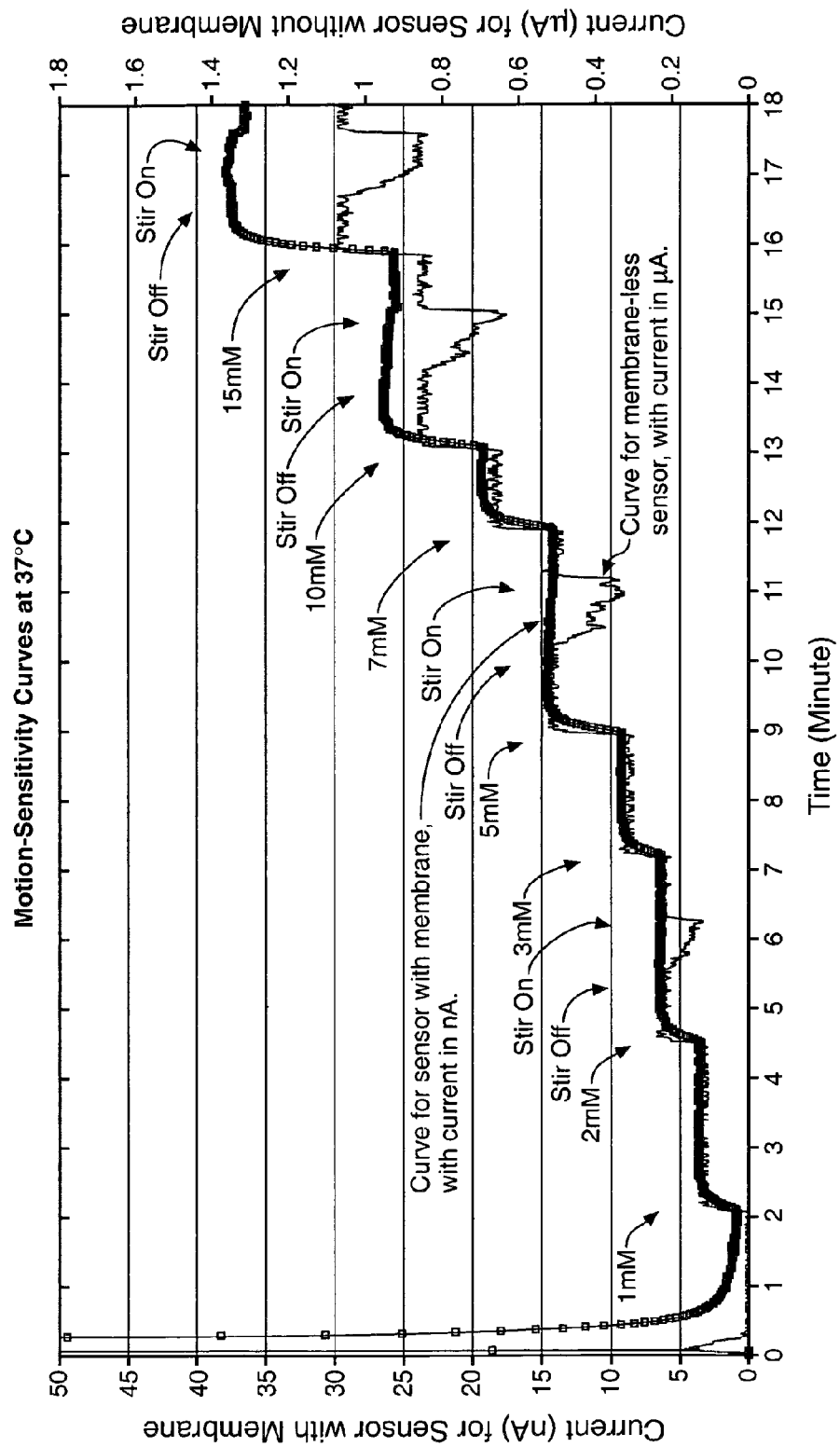
FIG. 6 is a graph of current output versus time at different levels of glucose concentration, with and without stirring, for a sensor having a glucose-diffusion-limiting membrane, according to the present invention, and for a sensor lacking such a membrane.

In this fourth example, a motion-sensitivity experiment was conducted in which a sensor A lacking a membrane was tested, and separately, a sensor B having a diffusion-limiting membrane according to the present invention was tested, all at 37° C. Sensor B had a membrane prepared from the same polymer and the same crosslinker as those of the sensors of Set 2 described in the calibration experiment above. In this experiment, for each of test, the sensor was placed in a beaker containing a PBS-buffered solution (pH 7) and a magnetic stirrer. The glucose concentration of the solution was increased in a step-wise manner over time, in much the same manner as described in the responsivity experiment above, as indicated by the various mM labels in FIG. 6. The stirrer was activated during each step-wise increase in the glucose concentration and deactivated some time thereafter, as illustrated by the "stir on" and "stir off" labels shown in FIG. 6. This activation and deactivation of the stirrer was repeated in a cyclical manner at several levels of glucose concentration and the output current of each of the sensors was measured throughout the experiment. The measured output currents (μA for sensor A; nA for sensor B) were plotted against time (minute), as shown in the motion-sensitivity graph of FIG. 6.

As shown, the output current for the membrane-less sensor A is greatly affected by the stir versus no stir conditions over the glucose concentration range used in the experiment. By contrast, the output current for sensor B, having diffusion-limiting membranes according to the present invention, is virtually unaffected by the stir versus no stir conditions up to a glucose concentration of about 10 mM, and only slightly affected by these conditions at a glucose concentration of about 15 mM. This result demonstrates the considerable stability of the membrane-equipped sensors of the present invention in both stirred and non-stirred environments. The stability of these membrane-equipped electrochemical sensors in an environment of fluid movement makes them ideal for analyte sensing within a moving body.

Sensor Reproducibility Experiment

Dip-coating, or casting, of membranes is typically carried out using dipping machines, such as a DSG D1L-160 of NIMA Technology of the United Kingdom. Reproducible casting of membranes has been considered quite difficult to achieve. (Chen, T., et al., *In Situ Assembled Mass-Transport Controlling Micromembranes and Their Application in Implanted Amperometric Glucose Sensors*, Anal. Chem., Vol. 72, No. 16, Pp. 3757-3763 (2000)) Surprisingly, sensors of the present invention can be made quite reproducibly, as demonstrated in the experiment now described.

Four batches of sensors (Batches 1-4) were prepared separately according to the present invention, by dipping the sensors in membrane solution three times using casting equipment and allowing them to cure. In each of the four batches, the membrane solutions were prepared from the polymer of Formula 4 and poly(ethylene glycol) diglycidyl ether (PEDGE) crosslinker having a molecular weight of about 200 (as in Set 2 and other Sets described above) using the same procedure. The membrane solutions for Batches 1 and 2 were prepared separately from each other, and from the membrane solution used for Batches 3 and 4. The membrane solution for Batches 3 and 4 was the same, although the Batch 3 and Batch 4 sensors were dip-coated at different times using different casting equipment. That is, Batches 1, 2 and 3 were dip-coated using a non-commercial, built system and Batch 4 was dip-coated using the above-referenced DSG D1L-160 system.

Calibration tests were conducted on each batch of sensors at 37° C. For each batch, the sensors were placed in PBS-buffered solution (pH 7) and the output current (nA) of each of the sensors was measured as the glucose concentration (mM) was increased. For each sensor in each of the four batches, a calibration curve based on a plot of the current output versus glucose concentration was prepared as shown in FIG. 7B (Batch 1: 5 sensors), FIG. 7C (Batch 2: 8 sensors), FIG. 7D (Batch 3: 4 sensors) and FIG. 7E (Batch 4: 4 sensors). The average slopes of the calibration curves for each batch were the following:

Batch 1: Average Slope=1.10 nA/mM (CV=5%);
Batch 2: Average Slope=1.27 nA/mM (CV=10%);
Batch 3: Average Slope=1.15 nA/mM (CV=5%); and
Batch 4: Average Slope=1.14 nA/mM (CV=7%).

Figure 7A:
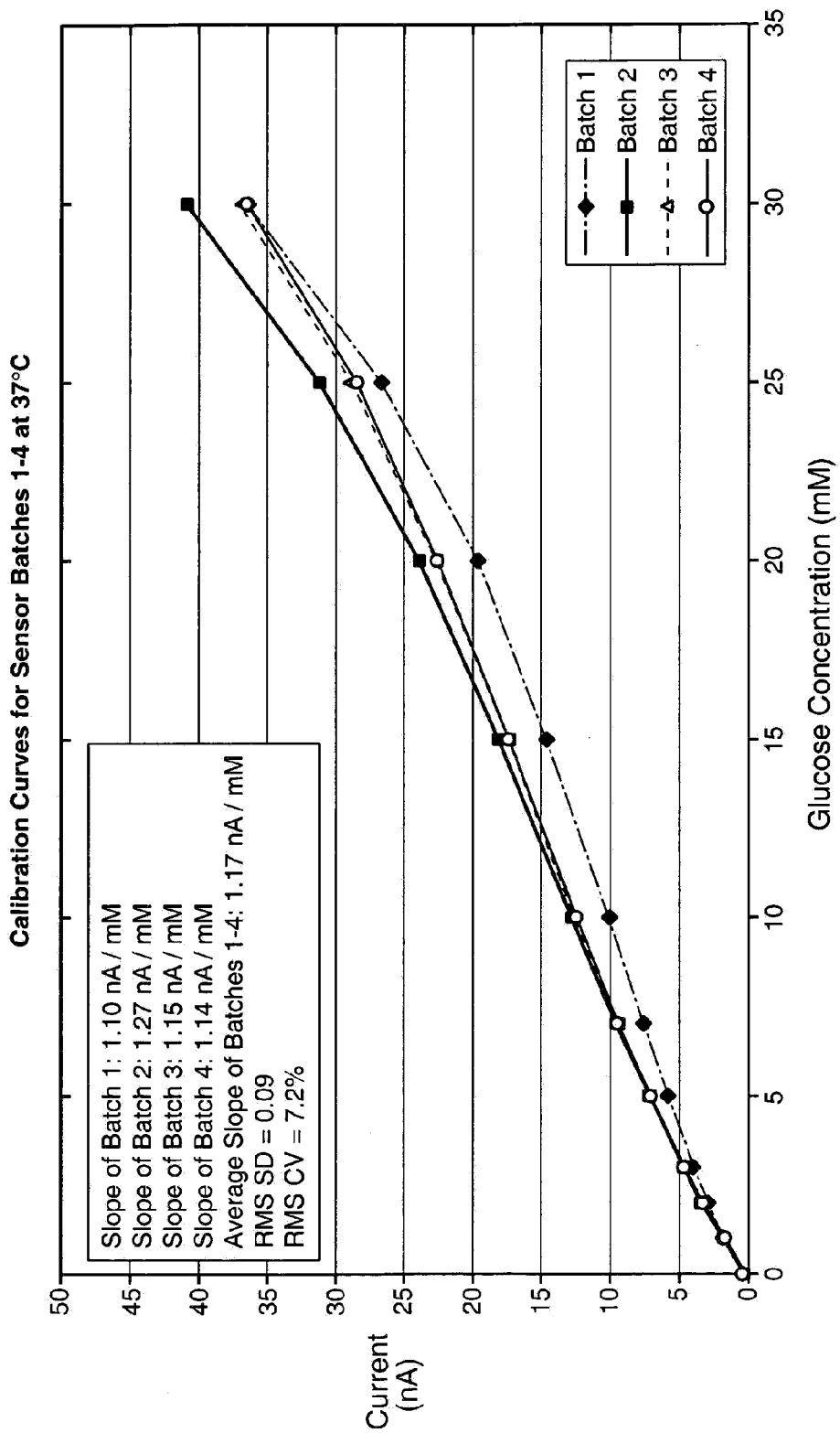
FIG. 7A is a graph of current output versus glucose concentration for four separately prepared batches of sensors having glucose-diffusion-limiting membranes, according to the present invention, based on average values.
Figure 7B:
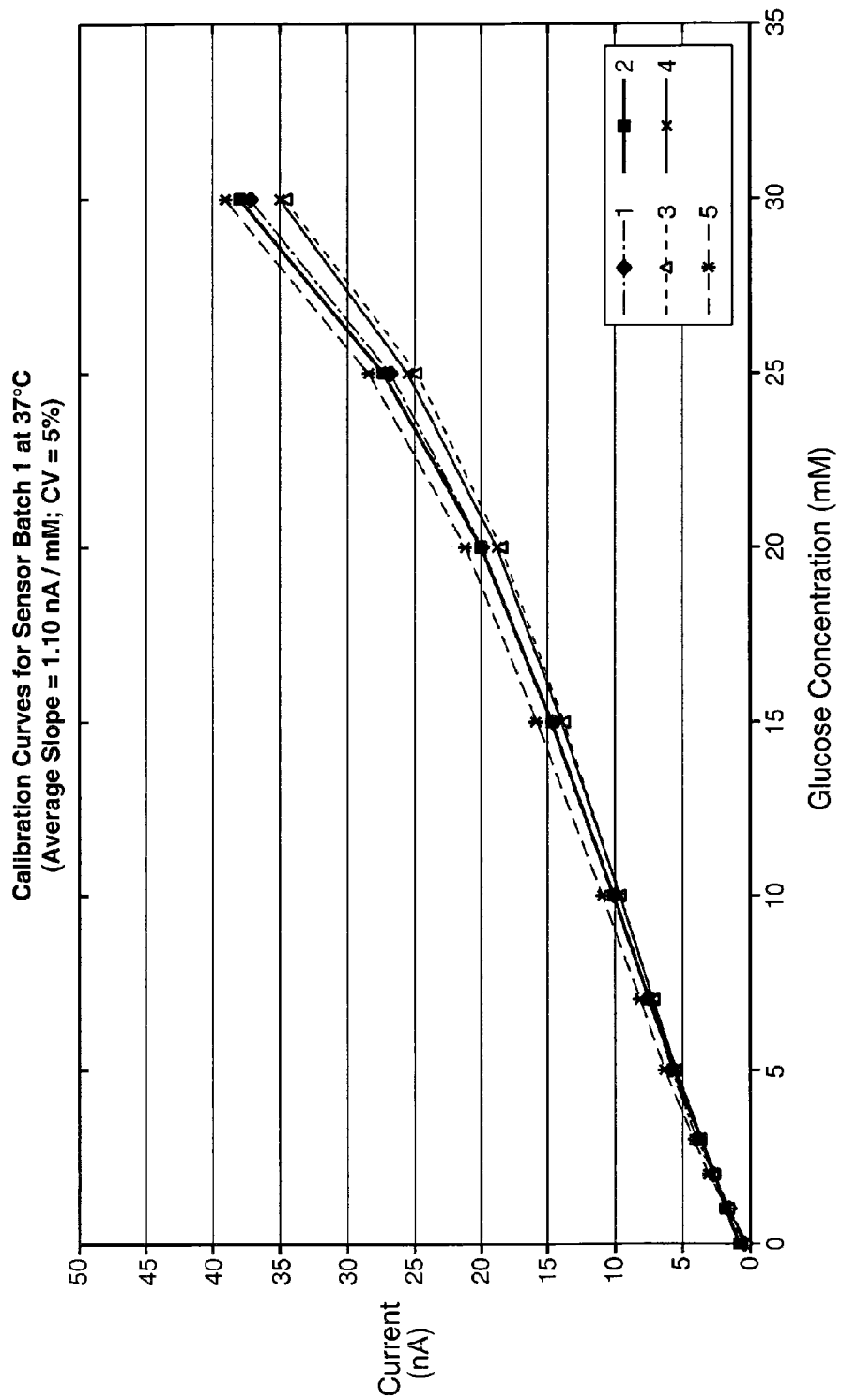
FIGS. 7B-7E are graphs of current output versus glucose concentration for individual sensors in each of the four above-referenced batches of sensors having glucose-diffusion-limiting membranes, respectively, according to the present invention. Herein, FIGS. 7A, 7B, 7C, 7D and 7E may be collectively referred to as FIG. 7.
Figure 7C:
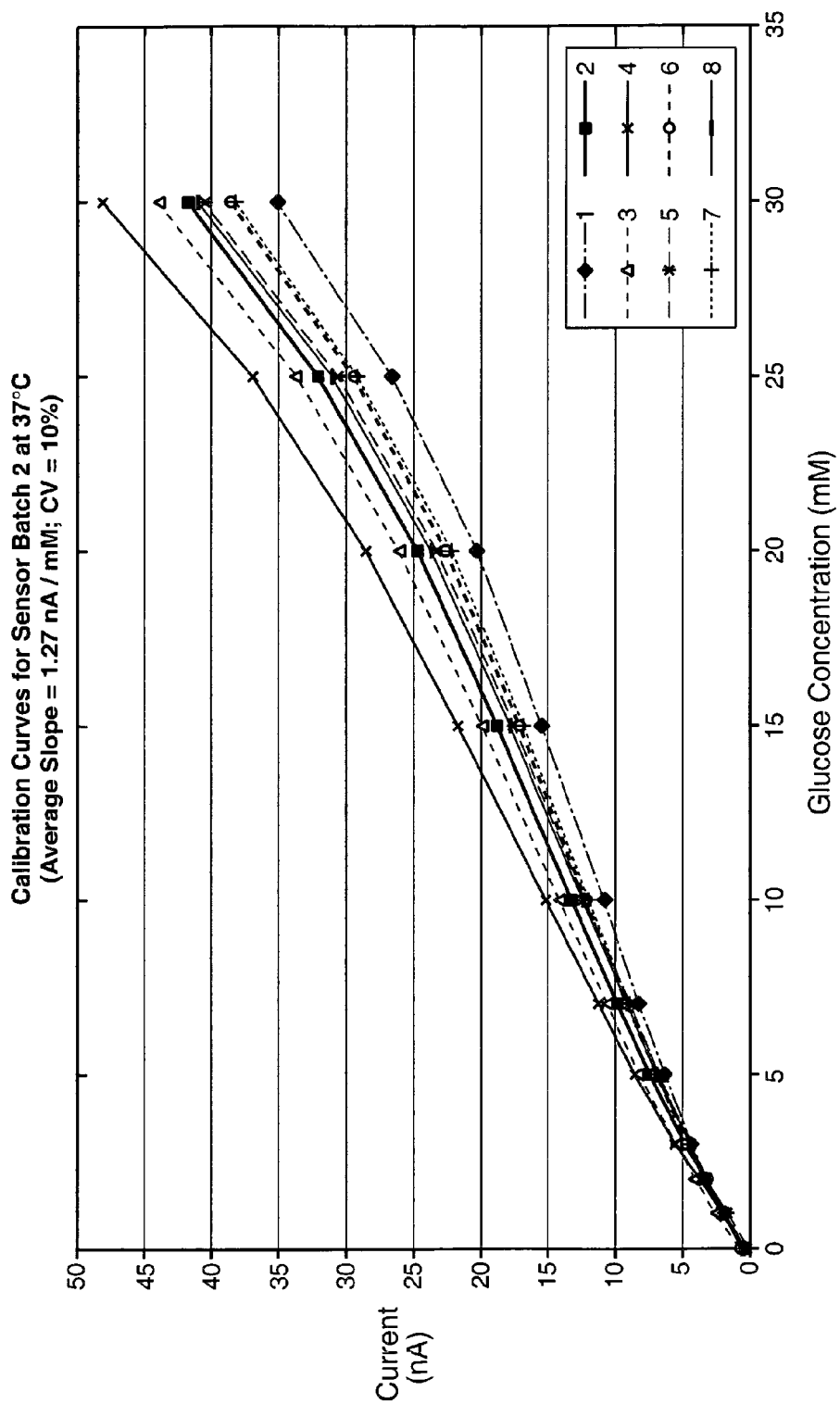
Figure 7D:
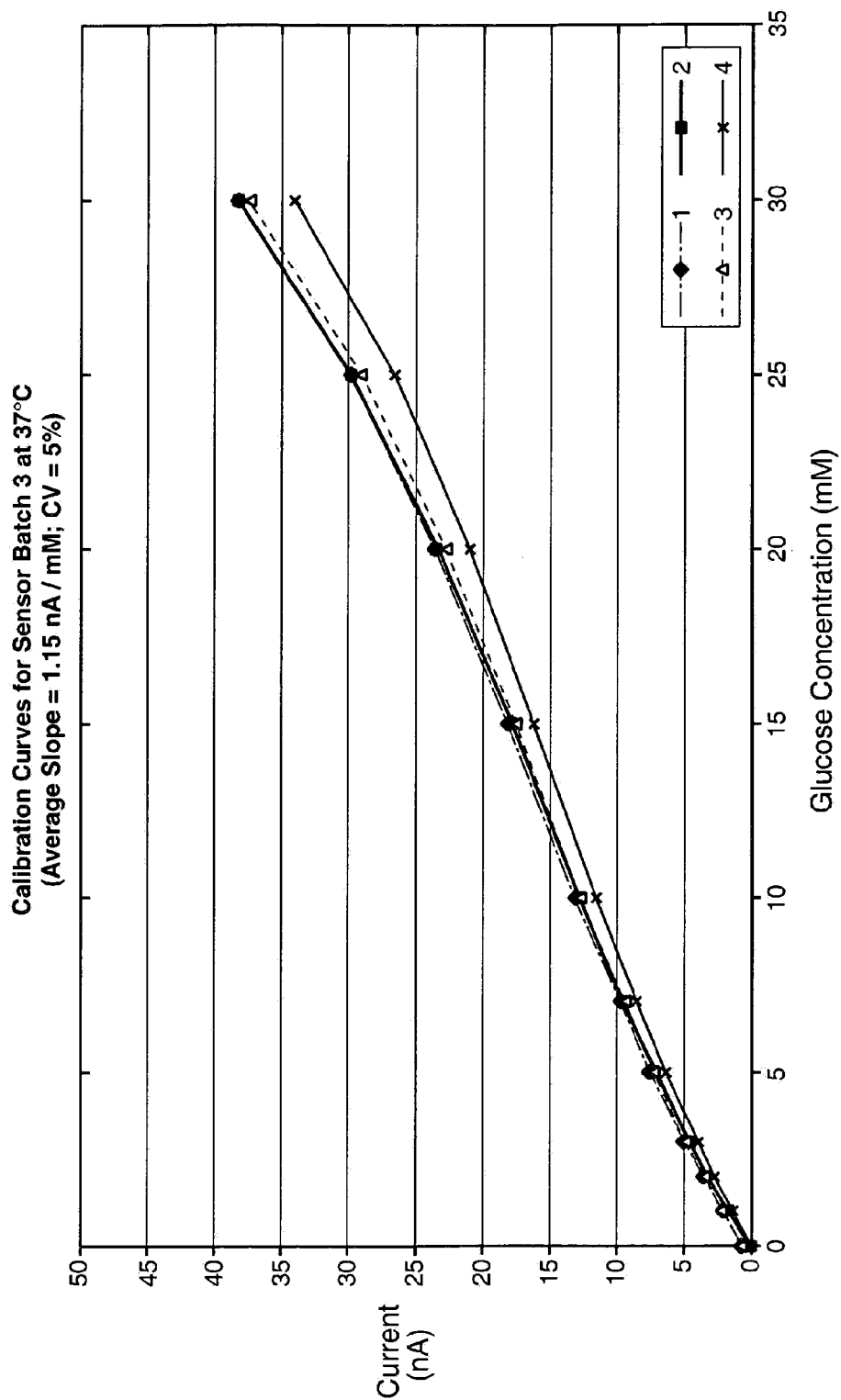
Figure 7E:
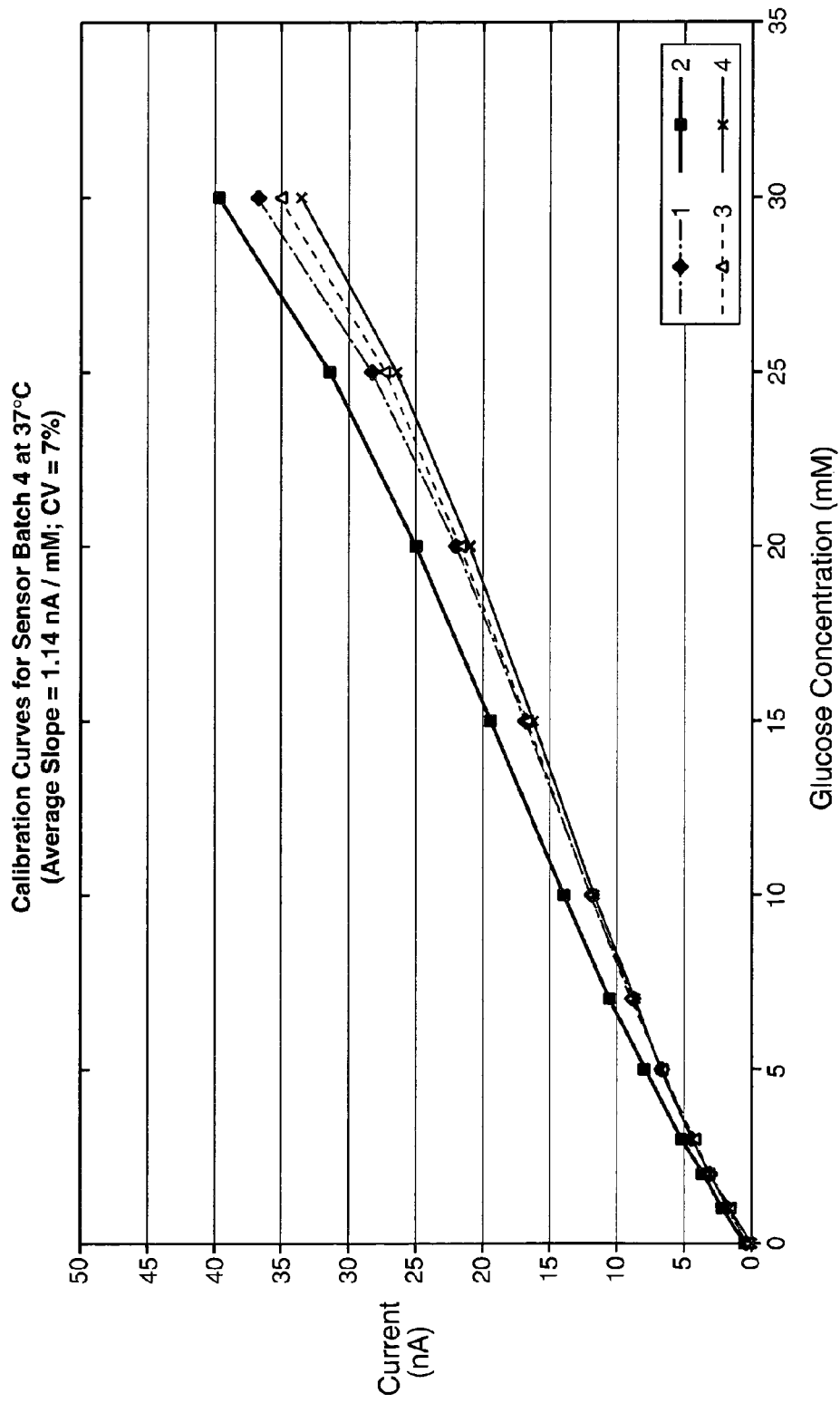

Further, for each batch, the current output for the sensors in the batch was averaged and plotted against glucose concentration, as shown in FIG. 7A. The average slope for Batches 1-4 was 1.17 nA/mM (CV=7.2%).

The slopes of the curves within each batch and from batch-to-batch are very tightly grouped, showing considerably little variation. The results demonstrate that sensors prepared according to the present invention give quite reproducible results, both within a batch and from batch-to-batch.

The foregoing examples demonstrate many of the advantages of the membranes of the present invention and the sensors employing such membranes. Particular advantages of sensors employing the membranes of the present invention include sensitivity, stability, responsivity, motion-compatibility, ease of calibration, and ease and reproducibility of manufacture.

Various aspects and features of the present invention have been explained or described in relation to beliefs or theories, although it will be understood that the invention is not bound to any particular belief or theory. Various modifications, processes, as well as numerous structures to which the present invention may be applicable will be readily apparent to those of skill in the art to which the present invention is directed upon review of the specification. Although the various aspects and features of the present invention have been described with respect to various embodiments and specific examples herein, it will be understood that the invention is entitled to protection within the full scope of the appended claims.

The invention claimed is:

1. A membrane structure comprising:
   an analyte responsive enzyme layer; and
   a membrane in contact with the analyte responsive enzyme layer, comprising a poly(4-vinylpyridine-co-styrene) polymer and a poly(ethylene glycol)-containing constituent.

2. The membrane structure of claim 1, wherein the poly(ethylene glycol)-containing constituent is a copolymer of polyethylene glycol and polypropylene glycol.

3. The membrane structure of claim 1, wherein the poly(ethylene glycol)-containing constituent is a polyether-amine.

4. The membrane structure of claim 1, wherein the analyte responsive enzyme layer further comprises a mediator.

5. The membrane structure of claim 1, wherein the analyte responsive enzyme layer further comprises a first polymer.

6. The membrane structure of claim 5, wherein the mediator is covalently bonded to the first polymer.

7. The membrane structure of claim 6, wherein the mediator forms one or more of carbon-carbon or carbon-nitrogen covalent bonds with the first polymer.

8. The membrane structure of claim 7, wherein the mediator is covalently bonded to the first polymer through a linker moiety.

9. The membrane structure of claim 6, wherein the mediator is covalently bonded to the first polymer through one or more ligands of the mediator.

10. The membrane structure of claim 9, wherein the one or more ligands comprises a substituted or unsubstituted heterocyclic nitrogen-containing moiety.

11. The membrane structure of claim 10, wherein the one or more ligands comprises a pyridine moiety or an imidazole moiety.

12. The membrane structure of claim 10, wherein the one or more ligands comprises a pyridine moiety and an imidazole moiety.

13. The membrane structure of claim 6, wherein the mediator comprises ruthenium or osmium.

14. The membrane structure of claim 1, wherein the analyte-responsive enzyme is a glucose-responsive enzyme.

15. The membrane structure of claim 14, wherein the glucose-responsive enzyme is glucose oxidase.

16. The membrane structure of claim 14, further comprising an enzyme cofactor.

17. The membrane structure of claim 16, wherein the enzyme cofactor is flavin adenine dinucleotide.

18. The membrane structure of claim 1, wherein the membrane further comprises a crosslinker.

19. The membrane structure of claim 18, wherein the crosslinker comprises an alkylating group selected from the group consisting of poly(ethylene glycol), poly(propylene glycol), a glycidyl group, aziridine, alkyl halide and sulfonate esters.

20. The membrane structure of claim 1, wherein the analyte response layer is disposed on a surface of an electrode.

* * * * *